US011612314B2

(12) United States Patent
Shin et al.

(10) Patent No.: US 11,612,314 B2
(45) Date of Patent: Mar. 28, 2023

(54) ELECTRONIC DEVICE AND METHOD FOR DETERMINING DEGREE OF CONJUNCTIVAL HYPEREMIA BY USING SAME

(71) Applicant: SAMSUNG ELECTRONICS CO., LTD., Suwon-si (KR)

(72) Inventors: Hyung Jong Shin, Suwon-si (KR); Min Soo Kim, Suwon-si (KR); Chun Ryu, Suwon-si (KR); Eun Jun Park, Suwon-si (KR); Chang Ho Ha, Suwon-si (KR); Sangchul Yoon, Seoul (KR); Haksu Kyung, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 295 days.

(21) Appl. No.: 16/759,463

(22) PCT Filed: Oct. 24, 2018

(86) PCT No.: PCT/KR2018/012635
§ 371 (c)(1),
(2) Date: Apr. 27, 2020

(87) PCT Pub. No.: WO2019/088555
PCT Pub. Date: May 9, 2019

(65) Prior Publication Data
US 2020/0337554 A1 Oct. 29, 2020

(30) Foreign Application Priority Data

Oct. 31, 2017 (KR) .................. 10-2017-0143227

(51) Int. Cl.
*A61B 3/107* (2006.01)
*G16H 30/40* (2018.01)
(Continued)

(52) U.S. Cl.
CPC ............ *A61B 3/107* (2013.01); *A61B 3/0025* (2013.01); *A61B 3/14* (2013.01); *A61B 5/02007* (2013.01);
(Continued)

(58) Field of Classification Search
CPC ........ A61B 2560/0431; A61B 5/02007; A61B 3/14; A61B 3/0025; A61B 3/107; G16H 30/40
See application file for complete search history.

(56) References Cited

U.S. PATENT DOCUMENTS 7,862,512 B2 * 1/2011 Iikubo .................. A61B 8/4218
600/459
8,687,862 B2 4/2014 Hsu et al.
(Continued)

FOREIGN PATENT DOCUMENTS

CN 101984916 3/2011
CN 103246883 8/2013
(Continued)

OTHER PUBLICATIONS

Partial Supplementary Search Report dated Jul. 8, 2020 in counterpart European Patent Application No. 18874834.7.
(Continued)

*Primary Examiner* — Mia M Thomas
(74) *Attorney, Agent, or Firm* — Nixon & Vanderhye, P.C.

(57) ABSTRACT

Disclosed are an electronic device and a method for determining a degree of conjunctival hyperemia using the same. The electronic device includes a camera and a processor configured to acquire an image including an eye captured by the camera, identify one or more blood vessels included in
(Continued)

the image, and determine a degree of conjunctival hyperemia based on sizes of the identified one or more blood vessels.

18 Claims, 25 Drawing Sheets

(51) Int. Cl.
  *A61B 3/00* (2006.01)
  *A61B 3/14* (2006.01)
  *A61B 5/02* (2006.01)

(52) U.S. Cl.
  CPC ...... *G16H 30/40* (2018.01); *A61B 2560/0431* (2013.01)

(56) References Cited

U.S. PATENT DOCUMENTS

| | | | |
|---|---|---|---|
| 9,554,117 | B2 | 1/2017 | Lee et al. |
| 9,931,171 | B1* | 4/2018 | Peyman ............... A61B 3/14 |
| 10,353,460 | B2* | 7/2019 | Shazly ............... A61B 5/1114 |
| 10,468,142 | B1* | 11/2019 | Abou Shousha ...... G16H 30/20 |
| 10,548,474 | B2* | 2/2020 | Dana ............... A61B 3/14 |
| 11,013,405 | B1* | 5/2021 | Karpecki ............ A61B 3/0033 |
| 2007/0055152 | A1* | 3/2007 | Ukubo ............... A61B 8/14 600/459 |
| 2007/0118045 | A1* | 5/2007 | Naghavi ............... A61B 5/01 600/549 |
| 2007/0225614 | A1* | 9/2007 | Naghavi ............... A61B 5/01 600/549 |
| 2010/0204584 | A1* | 8/2010 | Ornberg ............... G06T 7/0012 600/476 |
| 2011/0085138 | A1* | 4/2011 | Filar ............... A61B 3/145 351/206 |
| 2011/0164218 | A1* | 7/2011 | Ornberg ............... A61B 3/10 351/246 |
| 2013/0226008 | A1* | 8/2013 | Dana ............... G06T 7/0012 382/128 |
| 2014/0285436 | A1 | 9/2014 | Wu |
| 2015/0002373 | A1 | 1/2015 | Kobayashi et al. |
| 2017/0252466 | A1* | 9/2017 | Peyman ............... A61K 47/68 |
| 2019/0254515 | A1* | 8/2019 | Zhang ............... A61B 3/145 |
| 2019/0274536 | A1* | 9/2019 | Askarian ............... G06T 7/0016 |
| 2021/0085175 | A1* | 3/2021 | Wallace ............... G16H 50/70 |
| 2021/0113078 | A1* | 4/2021 | Hamrah ............... G06T 7/0012 |
| 2021/0321876 | A1* | 10/2021 | Zare Bidaki ............ A61B 3/14 |
| 2022/0079429 | A1* | 3/2022 | Chen ............... A61B 3/107 |
| 2022/0087524 | A1* | 3/2022 | Sasaki ............... G06T 7/20 |

FOREIGN PATENT DOCUMENTS

| | | | |
|---|---|---|---|
| CN | 103839054 | | 6/2014 |
| CN | 105208284 | | 12/2015 |
| CN | 112084961 A | * | 12/2020 ........... A61B 3/0016 |
| JP | 2006-015061 | | 1/2006 |
| JP | 5490477 | | 5/2014 |
| JP | 2015-177403 | | 10/2015 |
| KR | 10-2015-0019311 | | 2/2015 |
| KR | 10-1566618 | | 11/2015 |
| KR | 10-2017-0000027 | | 1/2017 |
| KR | 10-2017-0024361 | | 3/2017 |
| KR | 10-2017-0048072 | | 5/2017 |
| KR | 10-2017-0070470 | | 6/2017 |
| WO | WO-2021028858 A1 | * | 2/2021 ........... A61B 3/0025 |

OTHER PUBLICATIONS

Bouaoune Y et al., "Spatio-temporal characterization of vessel segments applied to retinal angiographic images," Pattern Recognition Letters, vol. 24, No. 1-3, Jan. 1, 2003, pp. 607-615.
Extended European Search Report dated Nov. 26, 2020 in counterpart European Patent Application No. 18874834.7.
Baudouin, Christophe et al., "The Measurement of Bulbar Hyperemia: Challenges and Pitfalls," European Journal of Ophthalmology, vol. 25, No. 4, May 21, 2015, pp. 273-279 (7 pages).
Abelson, Mark B et al., "Code Red: The Key Features of Hyperemia," Review of Ophthalmology, Apr. 22, 2010, 5 pages.
Perez-Cabre, Elisabet et al., "Image Processing of Standard Grading Scales for Objective Assessment Of Contact Lens Wear Complications," Proceedings of SPIE, Oct. 21, 2004, pp. 107-112 (7 pages).
Office Action dated Mar. 29, 2022 in Korean Patent Application No. 10-2017-0143227 and English-language translation.
Office Action dated Jun. 2, 2022 in Chinese Patent Application No. 201880066273.2 and English-language translation.
International Search Report for PCT/KR2018/012635 dated Feb. 25, 2019, 2 pages.
Written Opinion of the ISA for PCT/KR2018/012635 dated Feb. 25, 2019, 5 pages.
Office Action dated Jan. 5, 2023 in Chinese Patent Application No. 201880066273.2 and English-language translation.

* cited by examiner

ELECTRONIC DEVICE AND METHOD FOR DETERMINING DEGREE OF CONJUNCTIVAL HYPEREMIA BY USING SAME

This application is the U.S. national phase of International Application No. PCT/KR2018/012635 filed Oct. 24, 2018 which designated the U.S. and claims priority to KR Patent Application No. 10-2017-0143227 filed Oct. 31, 2017, the entire contents of each of which are hereby incorporated by reference.

BACKGROUND

Field

This disclosure relates to an electronic device and a method for determining a degree of conjunctival hyperemia by using the same. More particularly, the disclosure relates to an electronic device for determining a degree of conjunctival hyperemia in an image including the eye and a method for determining a degree of conjunctival hyperemia by using the same.

Description of Related Art

The conjunctival hyperemia means that the capillary vessel distributed over the conjunctiva is seen to be expanded by inflammation or stimulation. The hyperemia can occur by bacteria, virus infection and a variety of causes such as fine dust, pollen, and the like, coming into contact with the conjunctiva.

When the hyperemia is severe, a problem of deteriorating the eyesight with pain can occur. Accordingly, it is necessary to periodically check whether the conjunctival hyperemia occurs, and in the case of the occurrence of the hyperemia, it is necessary to get a medical treatment by visiting a hospital.

However, in the case of a related-art hyperemia-degree measuring device, it is common to calculate the hyperemia based on a ratio occupied by a red pixel value in an image capturing the eye. When calculating the hyperemia degree based on the red pixel value, however, if the hyperemia is not severe, there may be a problem in that it is not accurately determined whether the hyperemia has occurred. In the case of the related-art hyperemia measuring device, the hyperemia degree may be calculated based only on a total area of the eye and thus, there is a problem in that the hyperemia degree by parts of the eye may not be provided.

As for the related-art hyperemia measuring device, the hyperemia degree is analyzed from an image capturing the eye and only a result value thereof is provided to a user and thus, there is a problem in that the user may not trust the result value.

SUMMARY

The disclosure provides an electronic device capable of determining a hyperemia degree for each part of the eye, determining a hyperemia degree of a micro blood vessel, and enabling a user to trust a result value of analyzing the hyperemia degree, and a method for determining a degree of conjunctival hyperemia using the same.

An electronic device according to an embodiment may include a camera and a processor configured to obtain (or acquire) an image including an eye captured by the camera, identify (or extract) one or more blood vessels included in the image, and determine a degree of conjunctival hyperemia based on sizes of the identified one or more blood vessels.

The processor is configured to divide the plurality of blood vessels into a plurality of nodes based on a cross point of the plurality of blood vessels included in the image, and determine the degree of conjunctival hyperemia based on the sizes of the plurality of nodes, the plurality of nodes may be at least one of a blood vessel between the cross point and end points of each of the plurality of blood vessels with respect to the cross point and a blood vessel between the cross point and another cross point.

The processor is configured to calculate a hessian matrix of the image, apply the hessian matrix to the image, identify the plurality of blood vessels by binarizing the image to which the hessian matrix is applied, determine the cross point by converting a thickness of the plurality of blood vessels to a thickness of a predetermined unit, and calculate sizes of each of the plurality of nodes from the binarized image.

The processor is configured to acquire a sclera image in a predetermined unit area in the image, calculate sizes of the plurality of nodes based on cross points of the plurality of blood vessels included in the sclera image, and determine the degree of conjunctival hyperemia by comparing a sum of the calculated sizes of the plurality of nodes and the predetermined unit area.

The processor is configured to determine locations of the plurality of nodes in the image and determine a degree of hyperemia by parts of the eye based on locations in which the plurality of nodes are present.

The processor is configured to determine the degree of conjunctival hyperemia by determining a thickness of the plurality of nodes, acquire at least one node, among the plurality of nodes, having a thickness greater than or equal to a predetermined thickness, and calculating a size of the acquired at least one node, or determine the degree of conjunctival hyperemia by acquiring at least one node, among the plurality of nodes, having a thickness less than a predetermined thickness and calculating a size of the acquired at least one node.

The processor is configured to, based on a reflected light being included in the image, determine a remaining region, among the entire region of the image, other than the region including the reflected light, and determine the degree of conjunctival hyperemia based on a size of one or more blood vessels included in the remaining region.

The processor is configured to determine the degree of hyperemia by determining a remaining region except the detected one or more blood vessels from the image and further considering at least one of a color or a shape of the remaining region.

The processor is configured to sequentially provide an image captured by the camera, an image including a plurality of blood vessels divided into a plurality of nodes based on the cross point, and an image of the determined degree of hyperemia.

An eye image captured by the camera may include a left eye and a right eye of a user, and the processor is configured to, based on a distance between the left eye and the right eye being less than a predetermined distance, provide guide information causing the user to be positioned in proximity to the camera, and based on the distance between the left eye and the right eye included in the eye image being a predetermined distance, determine the degree of hyperemia.

The electronic device may further include an illuminance sensor, and the processor is configured to, based on an illuminance value sensed by the illuminance sensor being less than or equal to a predetermined illuminance value, provide guide information to lead adjustment of the illuminance value, and based on the illuminance value being greater than or equal to a predetermined illuminance value, determine the degree of conjunctival hyperemia included in the image.

The processor is configured to provide at least one of a cause of the degree of hyperemia and guide information for overcoming the degree of hyperemia based on at least one of state information of the electronic device and user information and the degree of hyperemia, the state information of the electronic device may be at least one of a distance between the electronic device and a user, a slope of the electronic device, an ambient illuminance of the electronic device, and time for using the electronic device, and the user information may be generated based on at least one of a photo application and a schedule application stored in the electronic device.

The electronic device may further include a storage, and the processor is configured to determine a change in the degree of hyperemia in a predetermined time unit based on the information on the degree of hyperemia stored in the storage and, based on the change in the degree of hyperemia being greater than or equal to a predetermined change amount, provide guide information for managing the degree of hyperemia.

The processor is configured to, based on an iris authentication application being executed, capture an image including the eye through the camera and determine the degree of conjunctival hyperemia from the captured image.

The processor may provide guide information guiding a position of the pupil to move to a predetermined position, and based on the pupil moving to the predetermined position, determine the degree of conjunctival hyperemia in the image including the eye.

The processor may, while the electronic device is operating in an unlock mode for unlocking a lock screen based on a movement of a pupil, based on the image including the eye being captured by the camera, determine the degree of conjunctival hyperemia from the image.

The electronic device further includes a storage and the processor may identify a user corresponding to the eye based on the user identification information, match the determined degree of hyperemia to the identified user, and store the same in the storage.

The processor may calculate an average value of the degree of conjunctival hyperemia by users based on information stored in the storage.

The processor may match and provide the calculated average value of the degree of hyperemia with each date on a calendar application execution screen.

The processor may provide the degree of conjunctival hyperemia as a graph by predetermined times based on information stored in the storage.

The electronic device may further include a communicator communicating with a server, and the processor may receive information on the degree of hyperemia of a plurality of users from the server, determine a ranking of the determined degree of conjunctival hyperemia based on the degree of hyperemia information of the plurality of users and provide the information on the ranking.

The processor may identify a user corresponding to the eye based on user identification information, receive information on at least one of age and occupation of each of the plurality of users from the server, divide the plurality of users into a plurality of groups based on at least one of age and occupation, determine a group to which the identified user of the plurality of groups belongs, and, provide the ranking information determined based on the degree of conjunctival hyperemia of a plurality of users belonging to the determined group.

According to an embodiment, a method for determining a degree of conjunctival hyperemia may include obtaining an image including an eye that is captured by a camera, identifying one or more blood vessels included in the image, and determining the degree of conjunctival hyperemia based on a size of the identified one or more blood vessels.

The determining the degree of hyperemia may include dividing the plurality of blood vessels into a plurality of nodes based on a cross point of the plurality of blood vessels included in the image, and determining the degree of the conjunctival hyperemia based on the size of the plurality of nodes, and the plurality of nodes may be at least one of blood vessels between end points of each of the plurality of blood vessels and blood vessels between the cross point and another cross point, with respect to the cross point.

The identifying the blood vessel may include calculating a hessian matrix of the image, applying the hessian matrix to the image, identifying the blood vessel by binarizing the image to which the hessian matrix is applied, and the determining the cross point may include determining by converting a thickness of the plurality of blood vessels to a thickness of a predetermined unit, and the determining the degree of hyperemia may include calculating sizes of each of the plurality of nodes from the binarized image.

The determining the degree of conjunctival hyperemia may include acquiring a sclera image in a predetermined unit area in the image, calculating sizes of the plurality of nodes based on cross points of the plurality of blood vessels included in the sclera image, and determining a degree of conjunctival hyperemia by comparing a sum of the calculated sizes of the plurality of nodes and the predetermined unit area.

The determining the degree of conjunctival hyperemia may include determining locations of the plurality of nodes in the image and determining a degree of hyperemia by parts of the eye based on locations in which the plurality of nodes are present.

The determining the degree of conjunctival hyperemia may include determining the degree of conjunctival hyperemia by determining a thickness of the plurality of nodes, acquiring at least one node, among the plurality of nodes, having a thickness greater than or equal to a predetermined thickness, and calculating a size of the acquired at least one node, or determining the degree of conjunctival hyperemia by acquiring at least one node, among the plurality of nodes, having a thickness less than a predetermined thickness and calculating a size of the acquired at least one node.

The determining the degree of conjunctival hyperemia may include, based on a reflected light being included in the image, determining a remaining region, among the entire region of the image, other than the region including the reflected light, and determining the degree of conjunctival hyperemia by calculating a size of one or more blood vessels included in the remaining region.

The determining the degree of conjunctival hyperemia may include determining the degree of hyperemia by determining a remaining region except the detected one or more blood vessels from the image and further considering at least one of a color or a shape of the remaining region.

The method may further include sequentially providing an image captured by the camera, an image including a plurality of blood vessels divided into a plurality of nodes based on the cross point, and an image of the determined degree of hyperemia.

The eye image captured by the camera may include a left eye and a right eye of a user, and the determining the degree of conjunctival hyperemia may include, based on a distance between the left eye and the right eye being less than a predetermined distance, providing guide information causing the user to be positioned in proximity to the camera, and based on the distance between the left eye and the right eye included in the eye image being a predetermined distance, determining the degree of hyperemia.

The determining the degree of conjunctival hyperemia may include, based on an illuminance value sensed by the illuminance sensor being less than or equal to a predetermined illuminance value, providing guide information to lead adjustment of the illuminance value, and based on the illuminance value being greater than or equal to a predetermined illuminance value, determining the degree of conjunctival hyperemia included in the image.

The method may further include providing at least one of a cause of the degree of hyperemia and guide information for overcoming the degree of hyperemia based on at least one of state information of the electronic device and user information and the degree of hyperemia, the state information of the electronic device may be at least one of a distance between the electronic device and a user, a slope of the electronic device, an ambient illuminance of the electronic device, and time for using the electronic device, and the user information may be generated based on at least one of a photo application and a schedule application stored in the electronic device.

The method may further include storing the determined degree of hyperemia, determining a change in the degree of hyperemia in a predetermined time unit based on the information on the degree of hyperemia stored in the storage and, based on the change in the degree of hyperemia being greater than or equal to a predetermined change amount, providing guide information for managing the degree of hyperemia.

The determining the degree of conjunctival hyperemia may include, based on an iris authentication application being executed, capturing an image including the eye through the camera and determining the degree of conjunctival hyperemia from the captured image.

The determining the degree of conjunctival hyperemia may include providing guide information guiding to move a positon of a pupil to a predetermined position, and based on the pupil moving to the predetermined position, determine the degree of conjunctival hyperemia from the image including the eye.

The processor may, while the electronic device is operating in an unlock mode for unlocking a lock screen based on a movement of a pupil, based on the image including the eye being captured by the camera, in response to the pupil included in the eye moving to a predetermined position, determine the degree of conjunctival hyperemia from the image.

The method may further include identifying a user corresponding to the eye based on user identification information, matching the determined degree of hyperemia with the identified user and storing the same in the storage.

The method may further include calculating an average value of the degree of conjunctival hyperemia based on a predetermined time by users based on information stored in the storage.

The method may further include matching the calculated average value of the degree of hyperemia to each date of the execution screen of a calendar application and providing the same.

The method may further include providing an average value of the degree of conjunctival hyperemia as a graph by predetermined times.

The method may further include receiving information on the degree of hyperemia of a plurality of users from a server, determining a ranking of the determined degree of conjunctival hyperemia based on the information on the degree of hyperemia of the plurality of users and providing information on the ranking.

The method may further include identifying a user corresponding to the eye based on user identification information, receiving information on at least one of age and occupation of each of the plurality of users from the server, dividing the plurality of users into a plurality of groups based on at least one of the age and occupation, determining a group, among the plurality of groups, to which the identified user belongs, and providing information on the determined ranking based on the information of the degree of conjunctival hyperemia of the plurality of users belonging to the determined group.

According to various embodiments, provided is an electronic device capable of determining the degree of hyperemia of each area of the eyes and determining the hyperemia degree of the fine blood vessels by determining the hyperemia degree based on the size of a plurality of nodes included in an image and a method for determining degree of conjunctival hyperemia using the same.

According to an embodiment, an electronic device that may analyze causes of hyperemia and may analyze diseases of related organs of the human body may be provided by determining a color and a shape of an area except the blood vessels. By sequentially displaying a process of determining the hyperemia degree, a user may trust the hyperemia degree determined by the electronic device.

DETAILED DESCRIPTION

The terms used in the present disclosure and the claims are general terms determined in consideration of the functions of the various example embodiments of the disclosure. However, these terms may vary depending on intention, technical interpretation, emergence of new technologies, and the like of those skilled in the related art.

Also, there may be some terms arbitrarily determined by an applicant. Unless there is a specific definition of a term, the term may be construed based on the overall contents and technological common sense of those skilled in the related art.

When it is decided that a detailed description for the known art related to the disclosure may unnecessarily obscure the gist of the disclosure, the detailed description will be omitted.

The embodiments have been described in detail with reference to the attached drawings and the descriptions of the drawings, but the disclosure is not limited by the embodiments.

Figure 1:
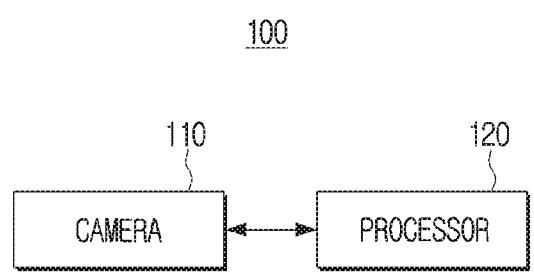
FIG. 1 is a block diagram illustrating an electronic device according to an embodiment.

FIG. 1 is a block diagram illustrating an electronic device according to an embodiment.

Referring to FIG. 1, an electronic device 100 may include a camera 110 and a processor 120. The electronic device 100 may be implemented as an electronic device including a camera. As an example, the electronic device 100 may be implemented as a smartphone. The embodiment is not limited thereto, and the electronic device 100 may be implemented as various electronic devices such as a tablet, a digital camera, a camcorder, a personal digital assistant (PDA), or the like.

The camera 110 may photograph a variety of subjects. The camera 110 may capture a user's eye. The camera 110 is capable of capturing the eye of a user including an anterior segment and a sclera.

The anterior segment refers to a front portion of the eye. Specifically, the anterior segment is the anterior segment of the eye and may include a cornea, the black part of the eye, a conjunctiva, a sclera, and crystalline lens.

The sclera is a white coat that covers almost every part of the eye and may mean the white part of the eye. The sclera may include a plurality of blood vessels.

The camera 110 may be implemented as a capturing device such as a capturing device (CMOS image sensor (CIS)) including a complementary metal-oxide semiconductor (CMOS) structure, a charged coupled device (CCD) structure, or the like. The embodiment is not limited thereto and the camera 100 may be implemented as a camera module of various resolutions capable of capturing a subject.

The processor 120 controls overall operations of the electronic device 100. For example, the processor 120 may control hardware or software components connected to the processor 120 by driving an operating system or an application program and perform data processing and algorithm. The processor 120 may load and process a command or data received from at least one of other components to a volatile memory, and store various data in a non-volatile memory.

The processor 120 may be implemented as a dedicated processor (e.g., an embedded processor) for performing the corresponding operations, or a generic-purpose processor (e.g., a central processing unit (CPU) or an application processor) that can perform the corresponding operations by executing one or more software programs stored in a memory device.

When the eye of a user is captured through the camera 110, the processor 120 may determine the degree of conjunctival hyperemia included in the captured image.

The processor 120 may acquire an image including the eye captured by the camera 110 and determine the degree of conjunctival hyperemia based on a cross point of a plurality of blood vessels included in an image.

Hereinbelow, with reference to FIGS. 2 to 5, the operation of the processor 120 will be described.

Figure 2:
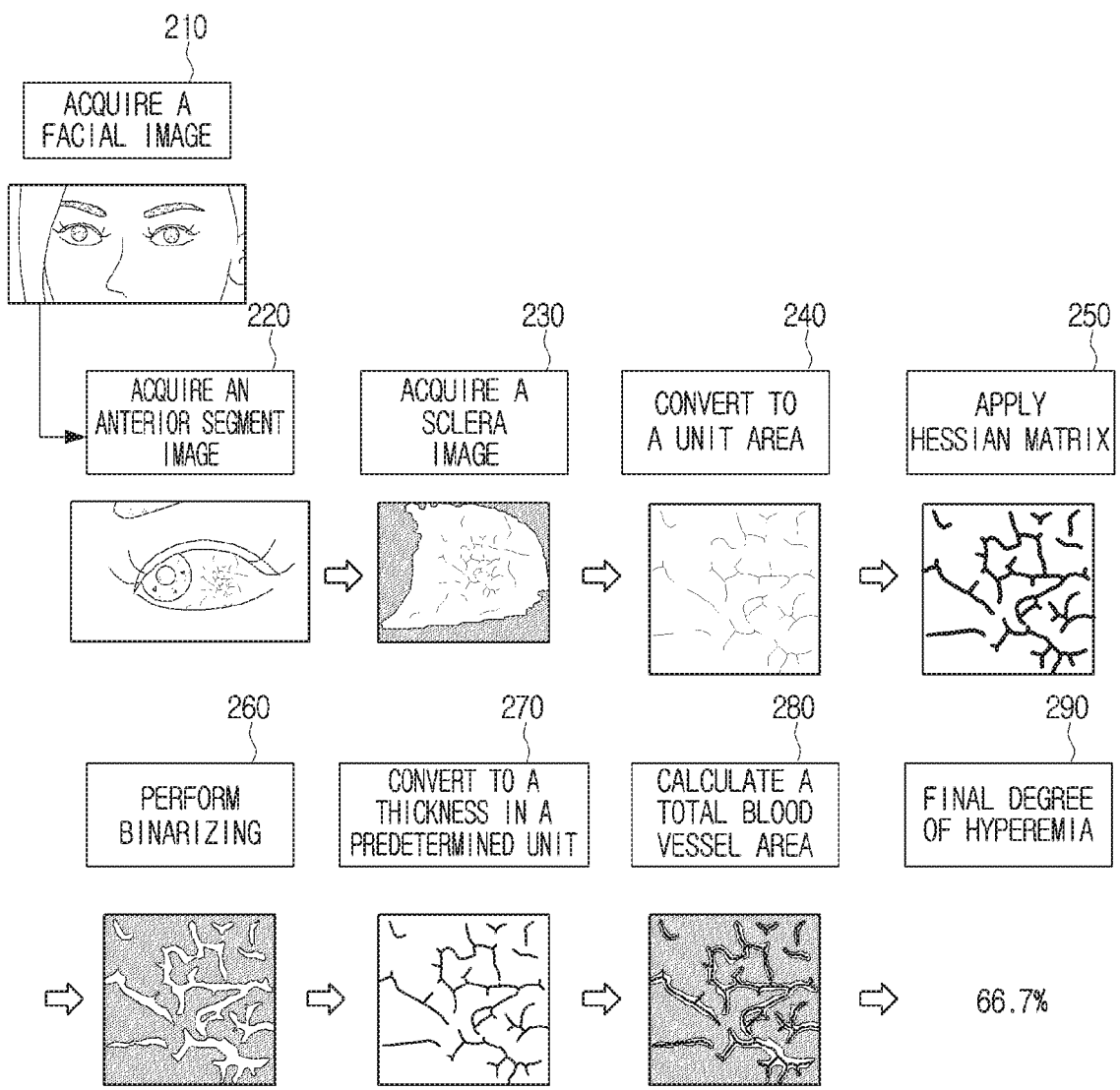
FIG. 2 is a diagram illustrating a method for determining a degree of hyperemia according to an embodiment.

FIG. 2 is a diagram illustrating a method for determining a degree of hyperemia according to an embodiment.

When the user's eye is captured through the camera 110, the processor 120 may generate an image 210 including the eye of the user. The captured image 210 may include nose, mouth, or the like, in addition to the eye.

The processor 120 may acquire an anterior segment image 220 from the captured image 210. The anterior segment is an anterior segment of the eye and may include a cornea, the black part of the eye, a conjunctiva, a sclera, and crystalline lens.

The processor 120 may acquire an anterior segment image using location information such as eyes, nose, mouth, etc. included in the captured image 210, or may acquire an anterior segment image by analyzing the density of the line after acquiring the edge information from the face included in the captured image 210. This is merely exemplary, and various techniques may be applied to the method by which the processor 120 acquires the anterior segment image 220. In one example, the processor 120 may acquire the anterior segment image via a deep learning technique based on a database.

The processor 120 may acquire a sclera image 230 from the anterior segment image 210. The sclera is a white color coat which covers most parts of the eye and means the white part of the eye.

Specifically, the processor 120 may acquire the sclera image by analyzing the pixel value of the anterior segment image 210 and then separating the pupil, the iris, and the sclera, or acquire the sclera image by analyzing the edge of the iris and then separating the sclera. The embodiment is not limited thereto and the processor 120 may acquire the sclera image by applying various techniques. In one example, the processor 120 may acquire the sclera image using a circular detection module (not shown) and may acquire the sclera image via a deep learning technique based on the database.

The processor 120 may convert the sclera image 230 in a predetermined unit area. The processor 120 may acquire the sclera image 240 that is converted in a predetermined unit area.

Here, the predetermined unit area can be set in consideration of the size of the eyes of a general user. For example, a predetermined unit area may be an area of a square having a width of 30 mm and a length of 30 mm The predetermined unit area may be, without limitation, changed according to a user setting.

The electronic device 100 may determine the degree of hyperemia of a plurality of users based on the same area.

The processor 120 may acquire a plurality of blood vessels from the sclera image 240 converted in a predetermined unit area.

The processor 120 may perform image processing for the sclera image 240 that has been converted into a predetermined unit area. Specifically, the processor 120 can adjust the white balance and contrast of the sclera image 240 by applying a contrast limited adaptive histogram equalization (CLAHE) algorithm to the sclera image 240. Here, the CLAHE algorithm refers to an algorithm for enhancing the contrast of an image by planarizing a histogram distribution level with respect to the brightness of an image. Accordingly, the processor 120 may obtain an image (not shown) in which the blood vessel in the sclera image is sharpened.

Thereafter, the processor 120 may calculate a Hessian matrix of the sclera image of which contrast is adjusted, and perform image processing for the sclera image based on the Hessian matrix. Accordingly, the processor 120 may acquire an image 250 in which a vascular part of the sclera image stands out. The processor 120 can binarize the sclera image 250 of which the vascular part stands out by the application of the Hessian matrix. Specifically, the processor 120 may binarize the blood vessel included in the sclera image 250 into a number 1, and binarize the remaining portion into a number 0. Accordingly, the processor 120 may acquire an image that is divided into a plurality of vascular areas and other areas, that is, a binarized sclera image 260.

Figure 3:
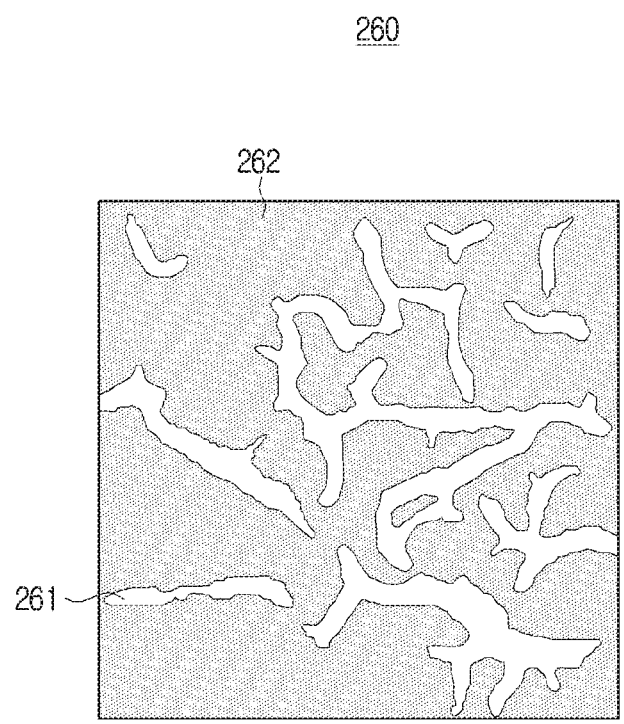
FIG. 3 is a diagram illustrating an image of a blood vessel of a binarized sclera according to an embodiment.

For example, referring to FIG. 3, the processor 120 may acquire the binarized sclera image 260 including a blood vessel area 260 which is binarized to number 1 and other areas 262 binarized to number 0.

The processor 120 may acquire a plurality of blood vessels from the binarized sclera image 260.

The processor 120 may divide the plurality of blood vessels included in the binarized sclera image 260 into a plurality of nodes. This is to determine the degree of conjunctival hyperemia by parts as well as the conjunctival hyperemia of the entire eye, based on the location and size of each of the plurality of nodes.

Each of the plurality of nodes may be a vessel between the end points of each of the plurality of blood vessels from the cross point of the plurality of vessels. However, it is not necessarily limited thereto, and in some cases, the node may be a vessel between the first cross point and the second cross point. Also, in the absence of the crossing vessels, the node may be a vessel itself.

The processor 120 may convert a plurality of blood vessels included in the binarized sclera image 260 to a predetermined unit thickness in order to divide the plurality of blood vessels into a plurality of nodes. Hereinafter, a description will be made with reference to FIG. 4.

Figure 4:
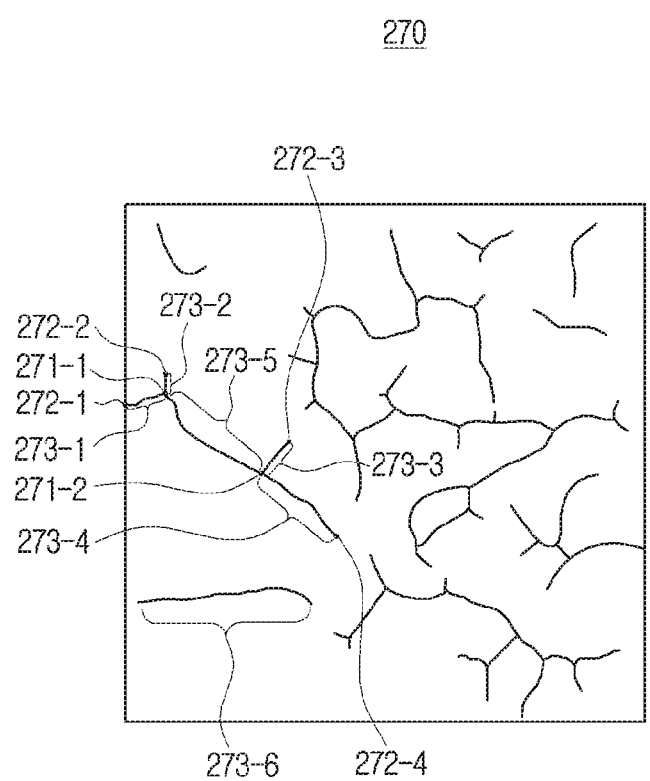
FIG. 4 is a diagram illustrating a method of dividing a plurality of blood vessels into a plurality of nodes according to an embodiment.

FIG. 4 is a diagram illustrating a method of dividing a plurality of blood vessels into a plurality of nodes according to an embodiment.

The processor 120 may convert the plurality of blood vessels included in the binarized sclera image 260 to a thickness in a predetermined unit. Here, the thickness in a predetermined unit is a thickness for determining the cross point of a plurality of blood vessels and may be set to 0.01 mm The predetermined thickness may be set differently by a user, without limitation.

The processor 120 may obtain a skeleton image 270 as illustrated in FIG. 4. For convenience of description, an image in which a plurality of blood vessels are converted to a thickness of a predetermined unit is referred to as the skeleton image 270.

The processor 120 may determine the cross point in which a plurality of blood vessels are crossed in the skeleton image 270.

For example, referring to FIG. 4, the processor 120 may determine a first cross point 271-1 in which a first blood vessel (a blood vessel between a point 272-1 and a point 271-1), and a second blood vessel (a blood vessel between a point 272-2 and a point 272-4) are crossed, and determine a second cross point 271-2 in which the second blood vessel and a third blood vessel (a blood vessel between a point 272-3 and a point 271-2) are crossed. The processor 120 may determine the cross point for the remaining plurality of blood vessels through the methods described above.

The processor 120 may determine the end points of each of the plurality of blood vessels in a skeleton image 270.

For example, referring to FIG. 4, the processor 120 may determine the end points 272-1 and 271-1 of the first blood vessel, the end points 272-2 and 272-4 of the second vessel, and the end points 272-3 and 271-2 of the third vessel. The processor 120 may determine the end points of each blood vessel through the method described above for the remaining plurality of blood vessels.

The processor 120 may divide a plurality of blood vessels into a plurality of nodes in the skeleton image 270.

For example, referring to FIG. 4, the processor 120 may determine the blood vessel from the end point 272-1 of the first blood vessel to the cross point 271-1 of the first and second blood vessels as a first node 273-1, determine a blood vessel from the end point 272-2 to the cross point 271-1 of the first and second blood vessels as a second node 273-2, and determine a blood vessel from the end point 272-3 of the third blood vessel to the cross point 271-2 between the second and third blood vessels as a third node 273-3, and determine the blood vessel from the end point 272-4 of the second blood vessel to the cross point 271-2 of the second and third blood vessels as a fourth node 273-4.

The processor 120 may determine the blood vessel from the first cross point 271-1 to the second cross section 271-2 as a fifth node 273-5, and may determine a blood vessel without a cross point as a sixth node 273-6.

The processor 120 may calculate a size of each of the plurality of nodes. Specifically, the processor 120 may calculate a size between the cross-points of the plurality of vessels in the binarized image 260 and the end points of each of the plurality of blood vessels based on the cross points.

For this purpose, the processor 120 may use an image 280 in which the skeleton image 270 is overlapped with the binarized sclera image 260. This will be described with reference to FIG. 5.

Figure 5:
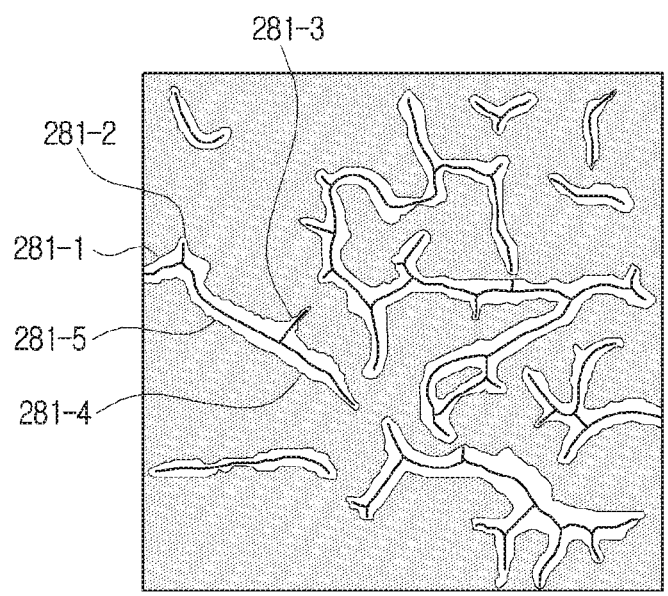
FIG. 5 is a diagram illustrating a method for calculating a size of each of a plurality of nodes according to an embodiment.

FIG. 5 is a diagram illustrating a method for calculating a size of each of a plurality of nodes according to an embodiment.

The processor 120 may overlap the skeleton image 270 with the binarized sclera image 260. Accordingly, the processor 120 may calculate the size of each of the plurality of nodes in the binarized sclera image 260. Hereinafter, for convenience of description, an overlapped image in which the skeleton image 270 is overlapped with the binarized sclera image 260 will be referred to as an overlap image 280.

The processor 120 may divide a plurality of blood vessels in the overlap image into a plurality of nodes. The processor 120 may divide a plurality of blood vessels in the overlap image 280 into a plurality of nodes based on each of the plurality of nodes determined in the skeleton image 270.

More specifically, the processor 120 may divide the skeleton image 270 into a plurality of areas to determine an area in which each of the plurality of nodes exists in the entire area of the skeleton image 270. The processor 120 may divide the overlap image 280 into a plurality of areas on the same basis as dividing the skeleton image 270 into a plurality of areas, and compare each area of the overlap image 280 with an area in which each of the plurality of nodes exists in the skeleton image 270 to determine an area in which each of the plurality of nodes exists among the entire area of the overlap image 280.

For example, referring to FIG. 5, the processor 120 may determine each of a first node to a fifth node 281-1 to 281-5 based on locations of each of the plurality of nodes determined in the skeleton image 270.

Accordingly, the processor 120 may calculate a size of each of the plurality of nodes in the overlap image 280. For example, in calculating the size of the first node 281-1, the processor 120 may generate in the first node 281-1 a plurality of virtual lines orthogonal with respect to the blood vessel of a predetermined thickness included in the first node in the first node 281-1, and add up the sizes of the generated plurality of lines to calculate the size of the first node 281-1.

However, this is merely exemplary, and the processor 120 may calculate each space by dividing the first node 281-1 into a plurality of triangles and squares, or calculate the respective spaces using point-counting. That is, various techniques can be applied to the method of calculating the size of each of the plurality of nodes. For each of the remaining nodes included in the overlap image 280, in addition to the first node 281-1, the processor 120 can calculate the size by the above-described method.

The processor 120 may determine the degree of conjunctival hyperemia included in the captured image based on the sizes of the plurality of nodes.

The processor 120 may compare the area of the sclera image 230 of a predetermined unit area with the size of the plurality of nodes to determine the hyperemia degree. More specifically, the processor 120 may compare the sum of the sizes of each of the plurality of nodes determined in the overlap image 280 with the area of the sclera image 230 of a predetermined unit area to determine the total hyperemia degree of the eye.

For example, if the area of the sclera image 230 of a predetermined unit area is 900 mm$^2$, and the sum of the sizes of each of the plurality of nodes is 600 mm$^2$, the processor 120 can calculate 290 the total hyperemia degree of the eye at 66.67% through the operation of (600÷900)×100.

In the above embodiment, it has been described that the degree of conjunctival hyperemia is determined by comparing the area of the sclera image 230 in a predetermined unit area and the sum of the sizes of each of the plurality of nodes, but the embodiment is not necessarily limited thereto.

For example, the processor 120 may determine the degree of conjunctival hyperemia by comparing the entire area of the sclera image 230 with the sum of the sizes of each of the plurality of nodes.

In the method of determining the hyperemia degree in the entire area of the sclera image 230, the technical spirit which is the same as the method of determining the hyperemia degree in the sclera image 240 in a predetermined unit area may be applied.

The processor 120 may perform image processing for the sclera image 230 itself and obtain a plurality of blood vessels included in the sclera image 230. The processor 120 can calculate the size of the plurality of nodes based on the cross point of the plurality of blood vessels, and compare the sum of the size of each of the calculated plurality of nodes and the total area of the sclera image 230 to determine a degree of conjunctival hyperemia.

The processor 120 may determine the degree of hyperemia by parts of the eye. This will be described with reference to FIG. 6.

Figure 6:
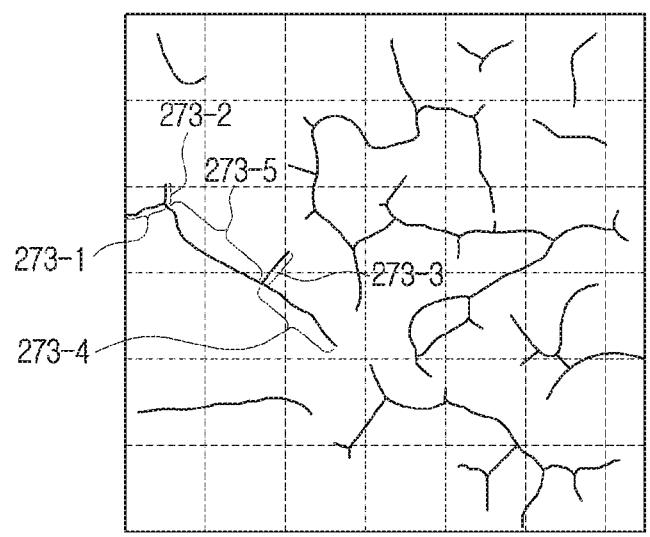
FIG. 6 is a diagram illustrating a method for determining a degree of hyperemia by parts of the eye according to an embodiment.

FIG. 6 is a diagram illustrating a method for determining a degree of hyperemia by parts of the eye according to an embodiment.

As described above, the processor 120 may divide the skeleton image 270 into a plurality of areas and may determine an area in which each of a plurality of nodes is present in the entire area of the skeleton image 270.

The processor 120 may divide the skeleton image 270 into a plurality of areas and coordinate each of the plurality of nodes included in the skeleton image 270 to determine an area in which each of the plurality of nodes is present.

For example, referring to FIG. 6, if the horizontal and vertical regions of the processor 120 are divided into a plurality of predetermined regions, the processor 120 may determine that a first node 273-1 is present in (1, 3)

coordinate region, determine that a second node 273-2 is present in (1, 3) coordinate region, that a third node 273-3 is present in (2, 4) and (2, 3) coordinate regions, and that a fourth node 273-4 is present in (2, 4) and (3, 4) coordinate regions. The processor 120 can determine the region in which each node is present for each of the remaining plurality of nodes included in the skeleton image 270, in the same manner as the method above.

The method described above is merely an exemplary, and the processor 120 may determine a region in which each of a plurality of nodes is present by various methods such as using relative locations of each of the plurality of nodes.

The processor 120 may determine the degree of hyperemia by parts of the eye based on a location in which each of the plurality of nodes is present. For example, the processor 120 may determine that hyperemia partially occurs only in a region in which each of the plurality of nodes is present.

The processor 120 may determine the degree of hyperemia by parts of the eye by further considering the sizes of each node calculated in the overlap image.

When it is determined that the size of a fifth node 271-5 is larger than the size of the first to fourth nodes 271-1 to 271-4, the processor 120 can determine that the degree of hyperemia of the region in which the fifth node 271-5 is present is higher than the degree of hyperemia of the region in which the first to fourth nodes 271-1 to 271-4 are present.

The processor 120 may determine the degree of conjunctival hyperemia based on the thickness of the blood vessels. This will be described with reference to FIGS. 7A to 7B below.

Figure 7A:
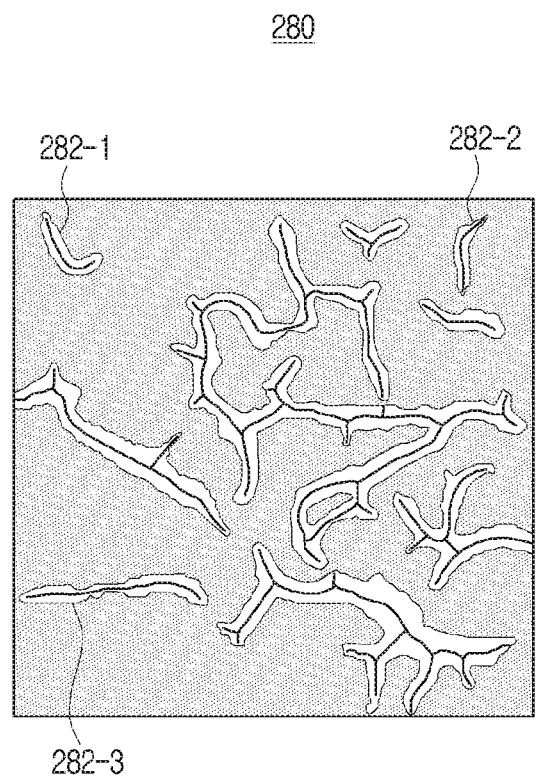
FIG. 7A is a diagram illustrating a method for determining a degree of conjunctival hyperemia based on a thickness of a blood vessel according to an embodiment.
Figure 7B:
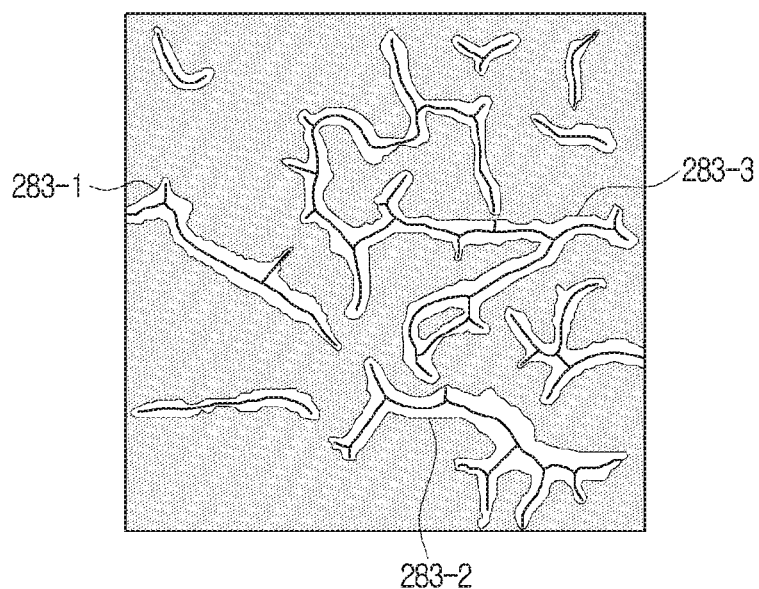
FIG. 7B is a diagram illustrating a method for determining a degree of conjunctival hyperemia based on a thickness of a blood vessel according to an embodiment.

FIGS. 7A and 7B are diagrams illustrating a method for determining a degree of conjunctival hyperemia based on a thickness of a blood vessel according to an embodiment.

The processor 120 may calculate the sizes of each node in the overlap image 280 as described above.

The processor 120 may determine at least one node that is less than a predetermined thickness among the plurality of nodes included in the overlap image 280. The predetermined thickness may be set to 0.05 mm, but is not necessarily limited thereto.

For example, referring to FIG. 7A, the processor 120 may determine blood vessels 282-1, 282-2, 282-3 that are made of a node less than a predetermined thickness. Here, the blood vessel having a thickness of less than a predetermined thickness can be a micro-vessel.

The electronic device 100 according to an embodiment may determine the degree of conjunctival hyperemia based on the micro-vessel.

The processor 120 may determine at least one node having a predetermined thickness or higher, among a plurality of nodes included in the overlap image 280. The predetermined thickness may be set to 0.05 mm, but is not necessarily limited thereto.

For example, referring to FIG. 7B, the processor 120 may determine blood vessels 283-1 and 283-2 that are made up of a predetermined thickness or more. Accordingly, the processor 120 may determine the degree of conjunctival hyperemia based on the remaining blood vessels except for the micro-vessel.

In the process of capturing the eye, reflected light can be included in the sclera image 240 due to the reflection of light, or the like. in this case, the processor 120 can determine the degree of conjunctival hyperemia, based on the remaining sclera region except for the region in which the reflected light is included, among the entire area of the sclera image 240. Hereinafter, a description will be made with reference to FIG. 8.

Figure 8:
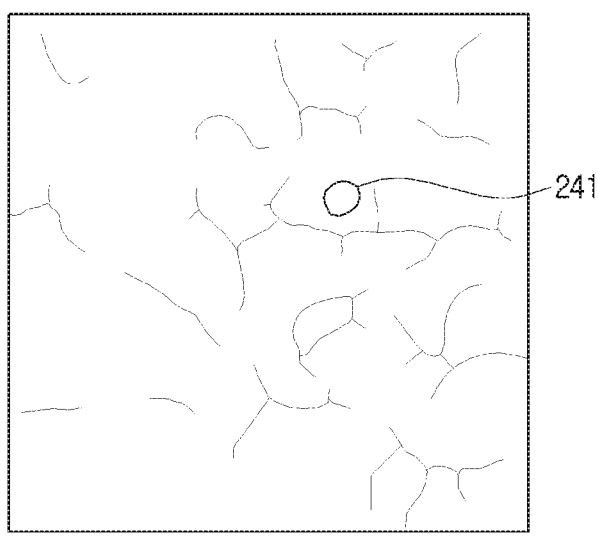
FIG. 8 is a diagram illustrating a method for removing reflected light and determining a degree of conjunctival hyperemia when reflected light is included in a sclera image according to an embodiment.

FIG. 8 is a diagram illustrating a method for removing reflected light and determining a degree of conjunctival hyperemia when reflected light is included in a sclera image according to an embodiment.

Referring to FIG. 8, a reflection light 241 may be included in a sclera image 240'. The region including the reflection light may be a region that is generated by the reflection of light in the process of capturing the eye.

The processor 120 may remove the reflection light from the sclera image 240'.

For this purpose, the processor 120 may first determine whether reflected light is included in the sclera image 240'. Specifically, if there is a region having a contrast that is greater than or equal to a predetermined brightness in an image 250 in which contrast is adjusted through the CLAHE algorithm, or the like, the processor 120 may determine the region as a region including the reflected light.

The processor 120 may exclude a region including the reflected light from the entire regions of the sclera image.

The processor 120 may determine the region including the reflected light from the image 250 in which the contrast is adjusted and may remove the reflected light 241 from the sclera image 240'.

The processor 120 may calculate the size of each node in the region in which the reflected light 241 is excluded from the sclera image 240' as the method described above and determine the degree of conjunctival hyperemia.

The electronic device 100 according to an embodiment may have an effect of accurately measuring the degree of conjunctival hyperemia even if reflected light is included in the captured image.

The processor 120 can determine the remaining area except for the blood vessel in the binarized image. That is, the processor 120 can determine the non-vascular region except the blood vessel area in the binarized image. Specifically, the processor 120 may determine a portion binarized to number 0 in the binarized image 260 as a non-vascular region.

The processor 120 may determine at least one of a color and a shape of the non-vascular region in an image prior to be performed with the image processing, that is, the sclera image 240 that has been converted into a unit area. The processor 120 can determine the color of the non-vascular region by determining the pixel value of the remaining region except the blood vessel, and can determine the shape of the non-vascular region by determining the shape of the remaining region except the blood vessel.

The processor 120 can determine the degree of hyperemia based on the non-vascular region. Specifically, the processor 120 may determine the ratio of red pixel values in the non-vascular region and determine the degree of hyperemia of the non-vascular region based thereon. Accordingly, the processor 120 can determine the redness phenomenon of the conjunctiva which is a representative allergic symptom. The processor 120 can determine a change in the color of the non-vascular region to determine whether there is a disease in the relevant organs of the human body such as anemia, jaundice, or the like.

The processor 120 may determine a change in a thickness of blood vessels based on a shape of the non-vascular region. The processor 120 may determine a blood vessel disease related to the change in the thickness of the blood vessels.

The processor 120 may visually feedback the process of determining the degree of conjunctival hyperemia into a user.

Figure 9:
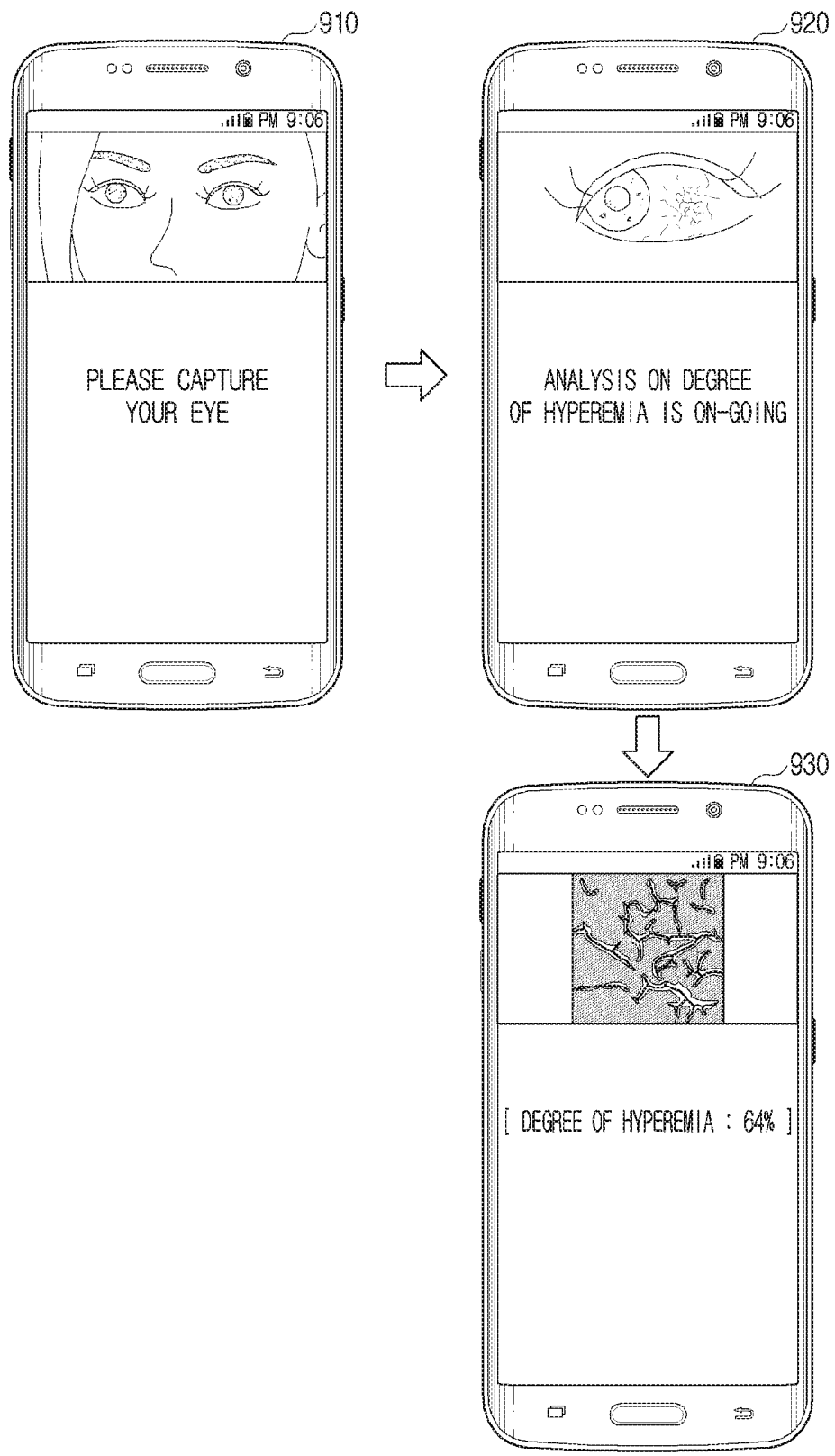
FIG. 9 is a diagram illustrating an embodiment of giving a visual feedback on a process of determining a degree of conjunctival hyperemia according to an embodiment.

FIG. 9 is a diagram illustrating an embodiment of giving a visual feedback on a process of determining a degree of conjunctival hyperemia according to an embodiment.

The electronic device 100 according an embodiment may visually feedback a process for determining the degree of conjunctival hyperemia. For this purpose, the electronic device 100 according to an embodiment may further include a display (not shown).

The display (not shown) may display a variety of images. The display may display an image capturing the eye of a user, an image including a plurality of blood vessels, divided into a plurality of nodes based on a cross point of the plurality of blood vessels, and an image for the degree of conjunctival hyperemia.

The display (not shown) may be implemented as various types of displays such as a liquid crystal display (LCD) panel, organic light emitting diodes (OLED), liquid crystal on silicon (LCoS), digital light processing (DLP), or the like. In the display 220, a backlight unit, a driving circuit that can be implemented as a type such an a-si thin film transistor (TFT), low temperature poly silicon (LTPS) TFT, organic TFT (OTFT), or the like, may be included.

As for a related-art electronic device, a degree of conjunctival hyperemia is determined and a result value thereof only is provided to a user. In this case, a user may not receive a feedback as to how the degree of hyperemia is calculated and thus, the user may not trust the result value.

Conversely, the electronic device 100 according to an embodiment may sequentially feedback a process of determining the degree of conjunctival hyperemia into a user so that the user may trust the result value.

For example, referring to FIG. 9, the processor 120 may display an image 910 captured through the camera 110.

The processor 120 may display an image 920 that is an image where the anterior segment is extracted from the captured image. The processor 120 may also display a message that the degree of hyperemia is being analyzed.

The processor 120 may display an image 930 including a plurality of blood vessels divided into a plurality of nodes based on the cross point of a plurality of blood vessels. The processor 120 may display the determined information on the degree of conjunctival hyperemia as well.

The user may receive a visual feedback that a plurality of blood vessels included in the captured image are acquired by the electronic device 100 and the degree of conjunctival hyperemia is measured based on the acquired blood vessels, and may have trust on the degree of conjunctival hyperemia that is the result value thereof.

In FIG. 9, it has been described that the captured image 910 by the camera, the image 920 extracting the anterior segment, and the image 930 including a plurality of blood vessels divided into a plurality of nodes are displayed but this is merely exemplary.

For example, besides the aforementioned images, the processor 120 may display all the images captured by the camera, the images obtained by applying the CLAHE algorithm to the captured image, the binarized images, the images obtained by obtaining the cross points and end points of the plurality of blood vessels in the binarized images, images for calculating the size of the blood vessels for each of the plurality of nodes, images for the determined level of hyperemia, or omit some of them.

Figure 10:
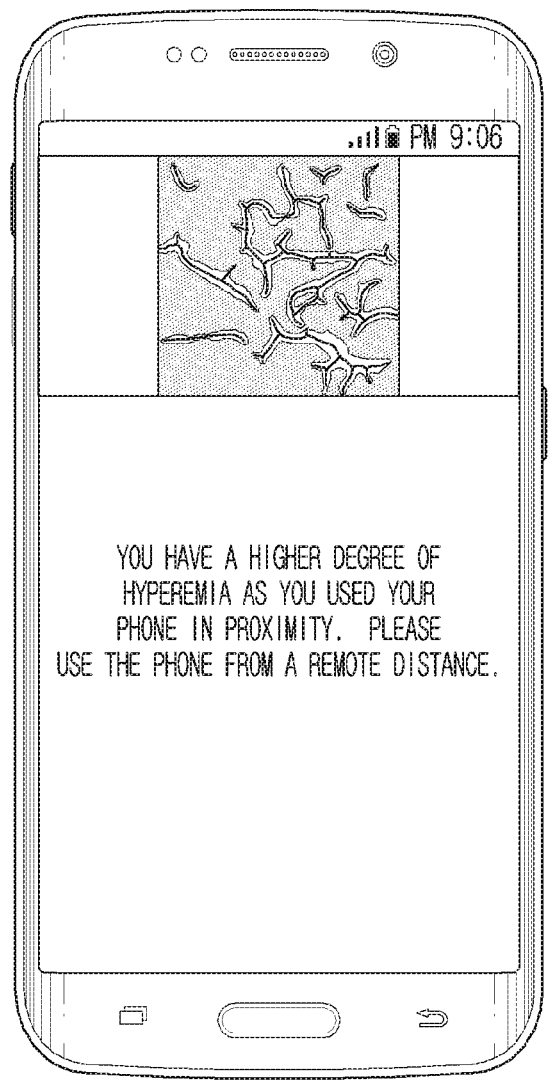
FIG. 10 is a diagram illustrating an embodiment of providing a cause of conjunctival hyperemia and guide information to overcome the hyperemia according to an embodiment.

FIG. 10 is a diagram illustrating an embodiment of providing a cause of conjunctival hyperemia and guide information to overcome the hyperemia according to an embodiment.

The processor 120 may provide causes of the conjunctival hyperemia and the guide information to overcome the conjunctival hyperemia.

For example, referring to FIG. 10, when the electronic device 100 is implemented as a smart phone, the processor 120 may display, via the display, the cause of the hyperemia that the degree of hyperemia has risen due to the user's close proximity to the smart phone, and may provide guide information that the smart phone needs to be used from the distance to resolve the hyperemia.

The processor 120 may use the state information of the electronic device 100. The state information condition of the electronic device may be at least one of a distance between the electronic device and the user, illuminance around the electronic device, or time for using the electronic device.

For this purpose, the processor 120 can calculate a distance between the electronic device 100 and the user by analyzing the image captured by the camera 110, and can determine a slope of the electronic device 100 through a gyro sensor. Further, the processor 120 can determine the ambient illuminance of the electronic device through the illuminance sensor.

If it is determined that the degree of hyperemia of the user is greater than or equal to a predetermined threshold value, the processor 120 can determine the cause of the hyperemia based on the state information of the electronic device 100 before measuring the degree of hyperemia. For example, if the distance between the electronic device 100 and the user is shorter than a predetermined distance prior to measuring the degree of hyperemia, the processor 120 can determine that the degree of hyperemia is risen because the user has used near the electronic device 100 in close proximity Accordingly, as shown in FIG. 10, the processor 120 may display the cause of the hyperemia that the degree of hyperemia has risen as the user used the smart phone in close proximity and the guide information to overcome the hyperemia that the smartphone needs to be used from the distance.

The processor 120 may provide the cause of the conjunctival hyperemia and guide information to overcome the hyperemia using the user information. The user information may be information generated based on at least one of a photo application and a schedule application stored in the electronic device 100.

Specifically, if the user's degree of hyperemia is determined to be greater than or equal to a predetermined threshold value, the processor 120 can determine the cause of the hyperemia based on the user information before measuring the degree of hyperemia. For example, the processor 120 may classify the image captured within a predetermined time from the point of time of measuring the degree of hyperemia in a photo application. If the classified image is an image of performing a work via computer, the processor 120 can determine that the conjunctival hyperemia has occurred due to the work via computer. In another embodiment, if a user's schedule is a video conference in a schedule application, the processor 120 may determine that the conjunctival hypermedia occurs due to the video conference.

The processor 120 may display the cause of the hyperemia that the degree of hyperemia has risen due to a work via computer and the video conference and the guide information that rest should be taken to overcome the hyperemia.

It has been exemplified that the determined degree of hyperemia is greater than or equal to a predetermined threshold value, but even when the determined degree of hyperemia is less than or equal to a predetermined threshold value, the aforementioned technical spirit can be applied.

When the determined degree of hyperemia is less than or equal to a predetermined threshold value, the processor 120 may determine the cause that the degree of hyperemia is not high based on at least one of the state information of the electronic device and the user information and display the same on the display.

For example, when the user uses an electronic device from distance before measuring the degree of hyperemia, a message that the degree of hyperemia is low as the user has used the electronic device from distance and guide information requesting that the distance from the electronic device needs to be maintained.

The processor 120 may analyze the cause of the hyperemia in consideration of the state information of the electronic device, user information, and the determined degree of hyperemia, and provide guide information to overcome the hyperemia.

For example, if it is determined that the user used a smart phone in a dark place, and if it is determined that the user has a video conference within a predetermined time from the time of measuring the degree of hyperemia, the processor 120 may provide the causes of hyperemia that the degree of hyperemia has risen due to the ambient brightness and video conference and guide information that the ambient brightness needs to be higher and the video conference needs to be stopped temporarily.

The processor 120 can determine the cause of hyperemia and guide information for overcoming the hyperemia through deep learning. More specifically, in a storage (not shown) of the electronic device 100, the degree of hyperemia information may be matched with each of the state information of the electronic device and the user information and stored therein. For example, the degree of hyperemia when the electronic device is used in a closer distance than a predetermined distance, the degree of hyperemia when the electronic device is used in the darker place than the predetermined illuminance, the degree of hyperemia when the user performs the work via computer for a predetermined time can be stored by learning.

Accordingly, after determining the degree of hyperemia of the user, the processor 120 can determine, of the information stored in the storage (not shown) through the deep learning, cause of the hyperemia and information for overcoming the degree of hyperemia, which correspond to the determined degree of hyperemia and the state information of the electronic device, and provide the information to the user. Similarly, the processor 120 may provide the cause of the hyperemia and information for overcoming the degree of hyperemia, corresponding to the determined degree of hyperemia and user information, through deep learning.

It has been described that the guide information is displayed on the display of the electronic device, but the guide information can be provided in a diverse manner For example, if it is determined that the determined degree of hyperemia is higher than a predetermined threshold value, the electronic device may output a warning sound through a speaker. If the electronic device does not have a display, the electronic device may transmit the guide information by communicating with the display device.

Figure 11:
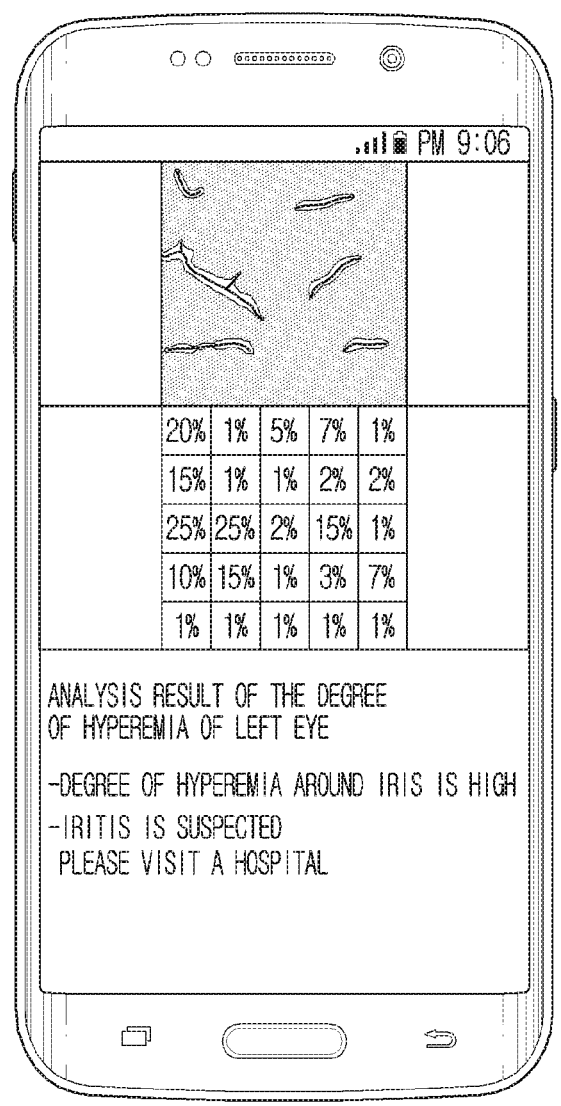
FIG. 11 is a diagram illustrating an embodiment of displaying a degree of hyperemia by parts of the eye according to an embodiment.

FIG. 11 is a diagram illustrating an embodiment of displaying a degree of hyperemia by parts of the eye according to an embodiment.

As described above, the processor 120 may determine the degree of hyperemia by parts of the eye based on locations in which each of the plurality of nodes is present. The processor 120 may display the determined degree of conjunctival hyperemia by parts through the display.

For example, referring to FIG. 11, the processor 120 may display the degree of hyperemia by parts of the eye in the overlap image 280 divided into a plurality of regions based on the locations in which each of the plurality of nodes are present and the sizes of each of the plurality of nodes.

In FIG. 11, the degrees of hyperemia by parts of the eye have been illustrated as separate tables, but according to an embodiment, the degree of hyperemia by parts of the eye may be overlapped with the overlap image and displayed.

The processor 120 may display information on disease of eyeball as well based on the determined degree of hyperemia by parts of the eye.

For example, if it is determined that the degree of hyperemia of the region around the iris is higher than the degree of hyperemia of another region, the processor 120 may display a message that the degree of hyperemia in a region around the iris is high along with a message that iritis is suspected. In another embodiment, if it is determined that the degree of hyperemia of a lower region of the sclera is higher than the degree of hyperemia of another region, the processor 120 may display a message that the drug allergy by eye drops is suspected.

The processor 120 may determine disease of eyeball based on a direction of each of the plurality of nodes, and display information about the disease of eyeball together. In one example, the processor 120 may also display a message that dryness is suspected if the direction of each of the plurality of nodes is in the horizontal direction.

The processor 120 may generate information on the disease of eyeball based on the sizes of each of the plurality of nodes, locations in which each node is present, and directionality of each node, and display the information.

The information on the ocular disease may be pre-stored in a storage (not shown) of the electronic device 100.

The electronic device 100 according to an embodiment may further include a communicator (not shown) capable of communicating with an external server, and may receive information about the ocular disease through communication with an external server. Specifically, the electronic device 100 may transmit information about the degree of hyperemia to an external server, and the external server may transmit information about the ocular disease determined based on the information of degree of hyperemia to the electronic device 100, and the electronic device 100 can display information about the ocular disease received from the external server.

The communicator (not shown) may further include a Wi-Fi chip, a Bluetooth chip, a wireless communication chip, or the like.

Figure 12A:
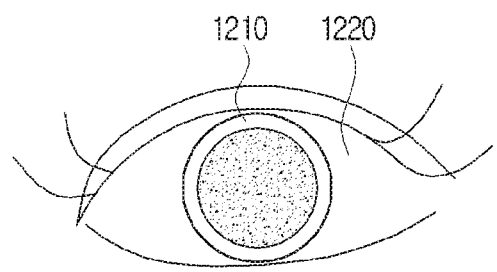
FIG. 12A is a diagram illustrating an embodiment of acquiring a region around the iris of the eye and a region other than the region around the iris, respectively, and determining the degree of hyperemia in each region according to an embodiment.
Figure 12B:
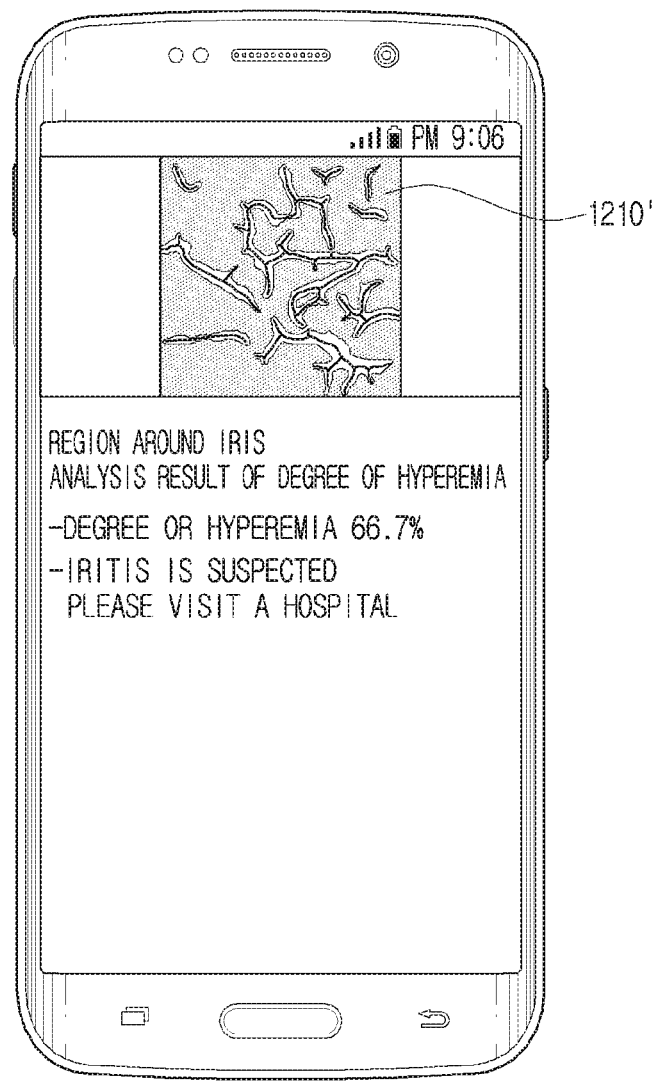
FIG. 12B is a diagram illustrating an embodiment of acquiring a region around the iris of the eye and a region other than the region around the iris, respectively, and determining the degree of hyperemia in each region according to an embodiment.
Figure 12C:
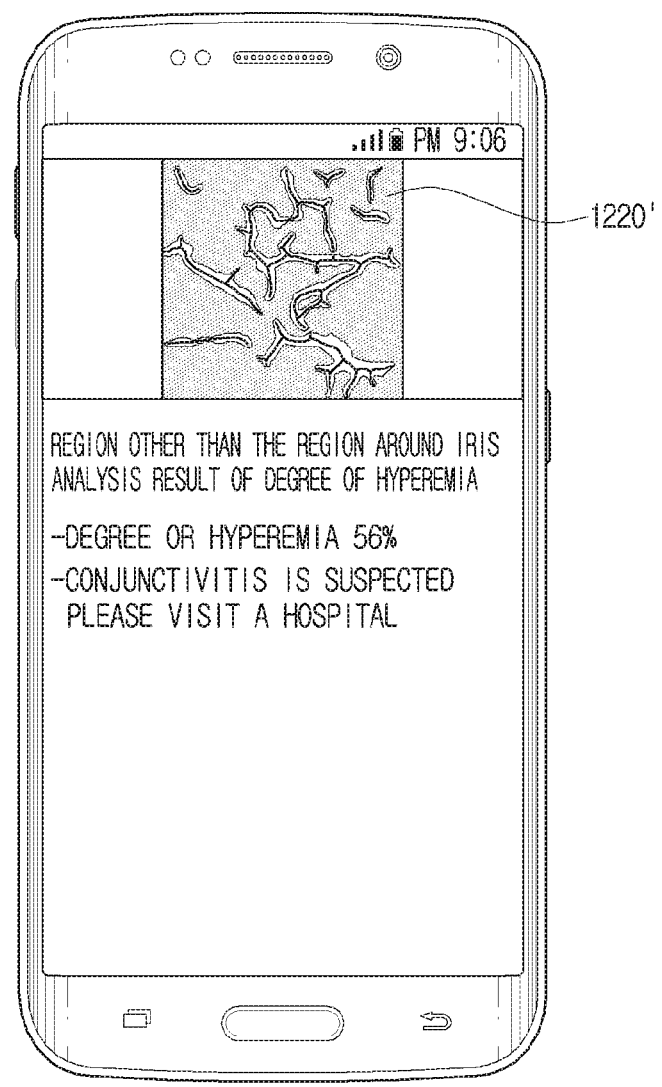
FIG. 12C is a diagram illustrating an embodiment of acquiring a region around the iris of the eye and a region other than the region around the iris, respectively, and determining the degree of hyperemia in each region according to an embodiment.

FIGS. 12A, 12B, and 12C diagrams illustrating an embodiment of acquiring a region around the iris of the eye and a region other than the region around the iris, respectively, and determining the degree of hyperemia in each region according to an embodiment.

Referring to FIG. 12A, the processor 120 may acquire a region 1210 around the iris of the eye and a region 1220 other than the region around the iris, respectively.

The processor 120 may analyze the pixel values of the anterior segment image 210 to separate the pupil, the iris, and the sclera and obtain the sclera image, as in the above-described embodiment. The processor 120 can obtain the region around the iris 1210 of the eye by analyzing the edge of the iris and determining the sclera image within a predetermined distance from the iris, and can obtain the region 1220 other than the region around the iris by excluding the region 1210 around the iris from the sclera image. However, the embodiment is not limited thereto, and the processor 120 may obtain each of the region 1210 around the iris and the region 1220 other than the region around the iris, respectively, through a deep learning technique based on a database.

As illustrated in FIGS. 12B and 12C, the processor 120 may determine the degree of hyperemia of each of the region 1210 around the iris and the region 1220 other than the region around the iris. In an image 1210' in which the region 1210 around the iris is converted to a predetermined unit area, the processor 120 can acquire the blood vessel through the image processing as described above, and determine the degree of hyperemia based on the size of each blood vessel and the size of the mode of the vessel. Accordingly, as shown in FIG. 12B, the processor 120 may provide the user with the result of determining the degree of hyperemia of the region 1210 around the iris.

In an image 1220' in which the region 1220 other than the region around the iris is converted to a predetermined unit area, the processor 120 can acquire the blood vessel through the image processing as described above, and determine the degree of hyperemia based on the size of each blood vessel or the size of the node of the blood vessel. Accordingly, as shown in FIG. 12C, the processor 120 can provide the user with the result of determining the degree of hyperemia of the region 1220 other than the region around the iris.

As described above, information on ocular disease may be provided more accurately by acquiring each of the region 1210 around the iris and the region 1220 other than the region around the iris the iris peripheral region 1220 and determining the degree of hyperemia of each region. For example, based on the degree of hyperemia determined in the region 1210 around the iris, the processor 120 may determine an ocular disease such as iritis and provide the user with the identification, and based on the degree of hyperemia determined in the region 1220 other than the region around the iris, the processor 120 may determine an ocular disease, such as a conjunctivitis, and provide the user with the identification.

Figure 13:
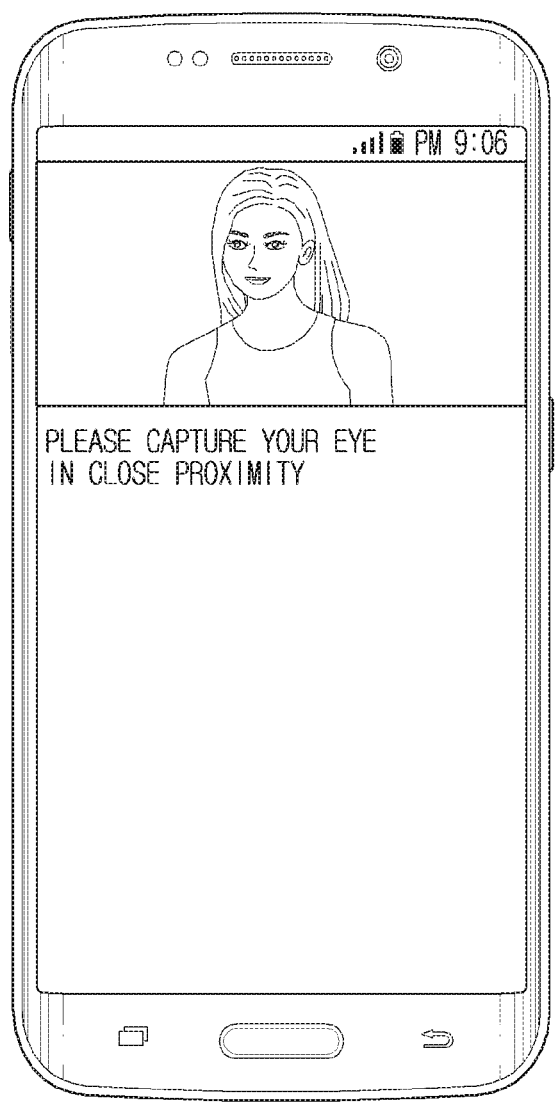
FIG. 13 is a diagram illustrating an embodiment of providing the guide information guiding to accurately measure the degree of conjunctival hyperemia according to an embodiment.

FIG. 13 is a diagram illustrating an embodiment of providing the guide information guiding to accurately measure the degree of conjunctival hyperemia according to an embodiment.

When the user captures the eye from a distance that is greater than or equal to a predetermined distance, a plurality of blood vessels may not be included in the captured image according to the resolution of the camera. The processor 120 may provide guide information guiding to accurately measure the degree of conjunctival hyperemia.

Referring to FIG. 13, an eye image captured by a camera may include a left eye and a right eye of a user. In this case, the processor 120 can determine the distance between the left eye and the right eye. Specifically, the processor 120 may determine whether the distance between the left eye and the right eye is less than a predetermined distance. Here, the predetermined distance can be set to about 65 mm When the distance between the left eye and the right eye determined in the captured image is less than a predetermined distance, the processor 120 may display the guide information inducting the user to be positioned in the proximity of the camera.

For example, referring to FIG. 13, the processor 120 may display a message inducting the user to capture the eye in close proximity to the camera.

Accordingly, if the related-art electronic device does not acquire the blood vessel in the captured image, capturing is requested again, causing a user inconvenience. Conversely, in the electronic device 100 according to an embodiment, if a user desires to capture the eye at a remote distance from the camera, guide information is displayed and thus, there is an effect to minimize user's inconvenience.

When the illuminance value around the electronic device 100 is less than or equal to a predetermined illuminance value, the processor 120 may provide the guide information guiding adjustment of the illuminance value.

For this purpose, the electronic device 100 may further include an illuminance sensor (not shown).

When an image including the eye is captured through the camera, the processor 120 may determine whether the illuminance value around the electronic device 100 is greater than or equal to a predetermined value and if the illuminance value is less than or equal to a predetermined illuminance value, the processor 120 may provide the guide information guiding adjustment of the illuminance value.

When the illuminance value is greater than or equal to a predetermined illuminance value, the processor 120 may determine the degree of conjunctival hyperemia included in the image.

This is because a blood vessel may not be included in an image captured below a predetermined illuminance value or a vessel may not be clearly revealed. Accordingly, it is possible to save power and prevent the load of the processor by preventing the degree of hyperemia to be unnecessarily analyzed.

Figure 14:
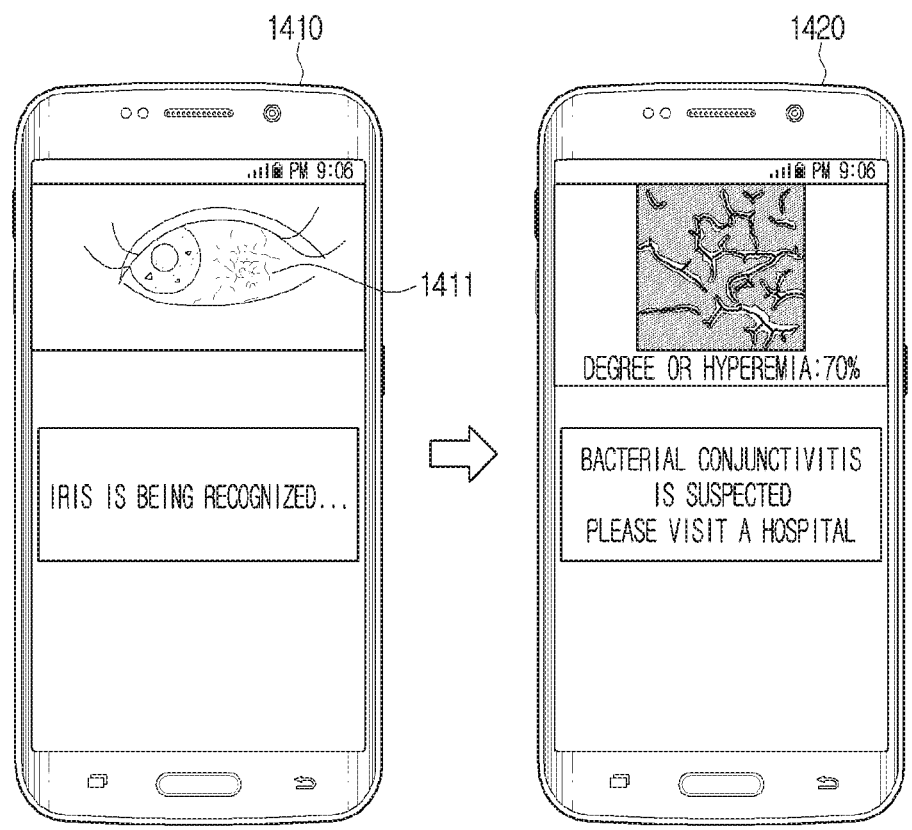
FIG. 14 is a diagram illustrating an embodiment of determining the degree of hyperemia in unlocking the lock screen through the iris authentication according to an embodiment.

FIG. 14 is a diagram illustrating an embodiment of determining the degree of hyperemia in unlocking the lock screen through the iris authentication according to an embodiment.

If the user attempts to unlock a screen through iris authentication, the processor 120 can determine the degree of conjunctival hyperemia included in the captured image. Specifically, when the user's eye is captured through the camera in the screen lock state, the processor 120 can analyze the iris in the captured image and, at the same time, determine the degree of conjunctival hyperemia in the manner described above.

Accordingly, the user may not need to execute a separate application for analyzing the degree of hyperemia and may receive an analysis result for the degree of hyperemia at the screen unlock stage.

When the iris authentication application is executed, the processor 120 can provide guide information for guiding the position of the pupil to a predetermined position. In one example, the processor 120 may provide guide information that requires moving the pupil in one of left and right directions.

When the pupil moves to a predetermined position, the processor 120 may determine the degree of conjunctival hyperemia in an image including the eye. In determining the degree of hyperemia, the processor 120 may repeatedly determine the degree of hyperemia based on the blood vessel present in the same sclera region.

For example, as shown in FIG. 14, the processor 120 may continue to determine the degree of hyperemia based on the blood vessels present in a left region 1411 of the eye. Accordingly, the electronic device 100 according to an embodiment can quantify the information of the degree of hyperemia by determining a change in the degree of hyperemia in the same sclera region. In addition, compared to the case where the pupil is located in the middle of the eye, a large area sclera image can be obtained, thereby the degree of hyperemia can be more accurately determined.

Figure 15:
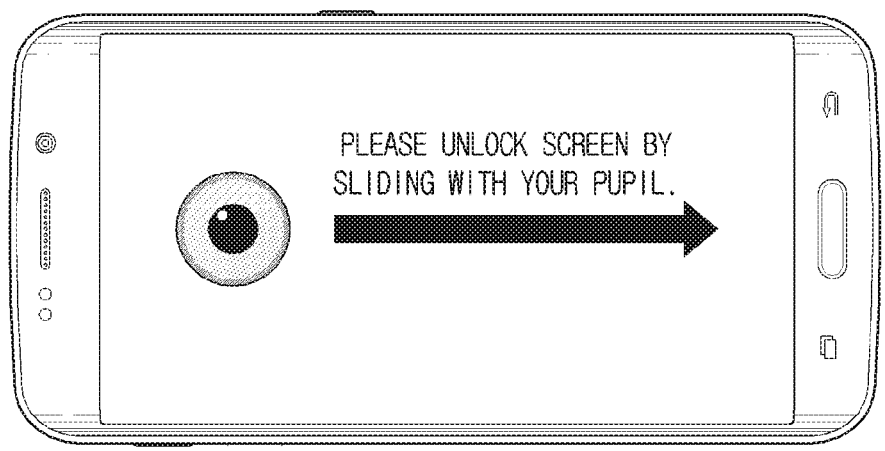
FIG. 15 is a diagram illustrating an embodiment of determining the degree of conjunctival hyperemia in unlocking the lock screen according to an embodiment.

FIG. 15 is a diagram illustrating an embodiment of determining the degree of conjunctival hyperemia in unlocking the lock screen according to an embodiment.

The electronic device 100 according to an embodiment may operate in a lock mode. The electronic device 100 may use a movement of the pupil to unlock the lock mode.

For example, referring to FIG. 15, the processor 120 may provide guide information guiding to unlock the screen by sliding with the eye. When an image including the eye is captured through a camera in a screen lock state, the processor 120 can determine the degree of conjunctival hyperemia in the captured image.

Accordingly, the user may have an effect of receiving an analysis result of the degree of hyperemia in the unlock stage without a need to execute a separate application for analyzing the degree of hyperemia.

When the pupil moves to a predetermined position, the processor 120 may determine the degree of conjunctival hyperemia. Accordingly, the processor 120 may determine the degree of hyperemia based on the blood vessel present in the same sclera region in determining the degree of hyperemia.

Accordingly, the electronic device according to an embodiment of the present invention can determine the degree of hyperemia in the same sclera region. In addition, compared to the case where the pupil is located in the middle of the eye, a large area sclera image can be obtained, thereby more accurately determining the degree of hyperemia.

Figure 16:
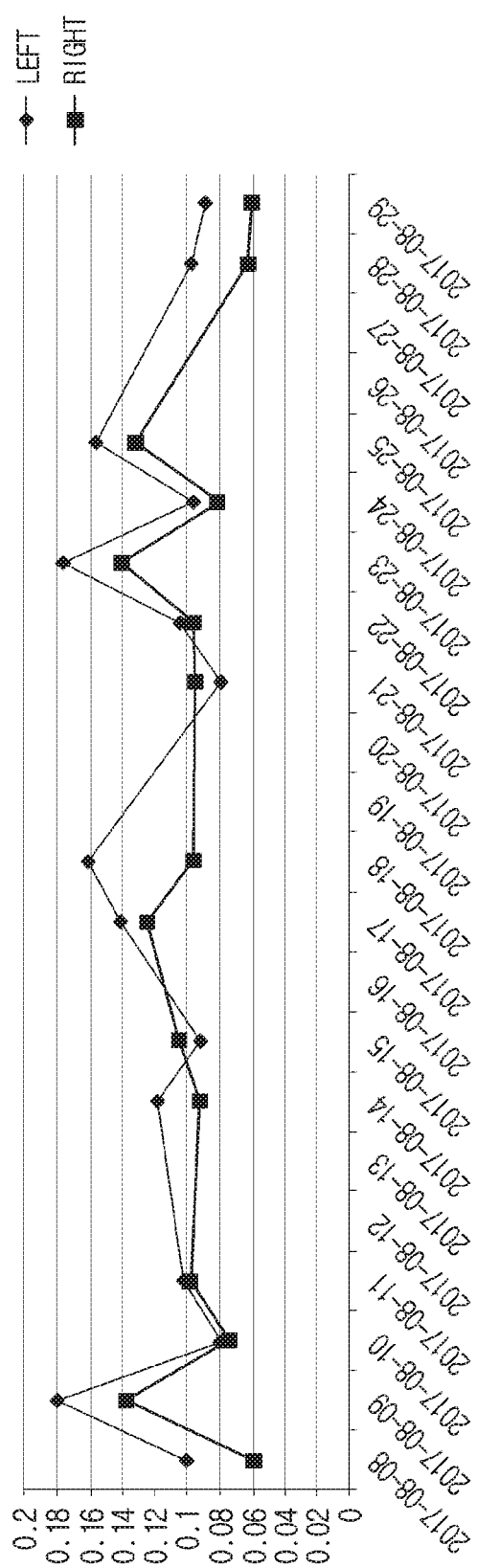
FIG. 16 is a diagram illustrating an embodiment of providing the degree of hyperemia graph according to an embodiment.

FIG. 16 is a diagram illustrating an embodiment of providing the degree of hyperemia graph according to an embodiment.

The processor 120 may determine the degree of conjunctival hyperemia, and store the result value in a storage (not shown). The processor 120 can calculate an average value of the degree of conjunctival hyperemia based on a predetermined time. For example, the processor 120 may calculate an average value of the degree of conjunctival hyperemia in a daily unit.

The processor 120 may provide an average value of the calculated degree of conjunctival hyperemia. For example, referring to FIG. 16, the processor 120 may calculate an average value of the degree of conjunctival hyperemia on a daily basis, and provide an average value of the degree of conjunctival hyperemia as a graph on a daily basis. Accordingly, the user can easily grasp the change of the degree of hyperemia.

The processor 120 can determine a user corresponding to an eye included in the captured image based on the user identification information, match the degree of hyperemia determined through an image to an identified user, and store the same in the storage.

The user identification information may be a user identification (ID) information, iris information, or the like, but is not limited thereto.

The processor 120 may calculate an average value of the degree of conjunctival hyperemia by users and provide a graph of the degree of conjunctival hyperemia by users.

Figure 17:
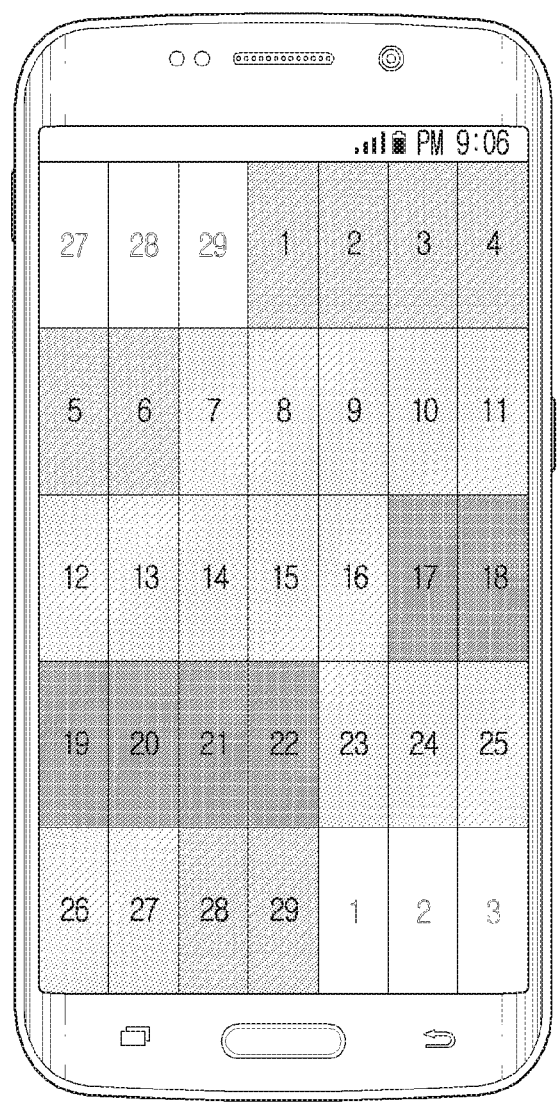
FIG. 17 is a diagram illustrating an embodiment of displaying the degree of conjunctival hyperemia in a calendar application execution screen according to an embodiment.

FIG. 17 is a diagram illustrating an embodiment of displaying the degree of conjunctival hyperemia in a calendar application execution screen according to an embodiment.

The processor 120 may calculate an average value of the degree of conjunctival hyperemia as described above. For example, the processor 120 may calculate an average value of the degree of conjunctival hyperemia on a daily basis.

The processor 120 may provide an average value of the degree of conjunctival hyperemia calculated on a daily basis by matching the average value to each date on the application execution screen.

For example, referring to FIG. 17, the processor 120, based on a predetermined threshold value, may differentiate a color on a date when the degree of hyperemia is higher than a predetermined threshold value from a color on a date when the degree of hypermedia is lower than a predetermined threshold, and display the same on the calendar application execution screen. However, this is only one embodiment, and the processor 120 may display the calculated average value itself on each date of the execution screen of the calendar application.

The user may not only easily grasp the tendency of the change in the degree of hyperemia but also may easily receive a visual feedback on a date where the average value is high or low.

Figure 18:
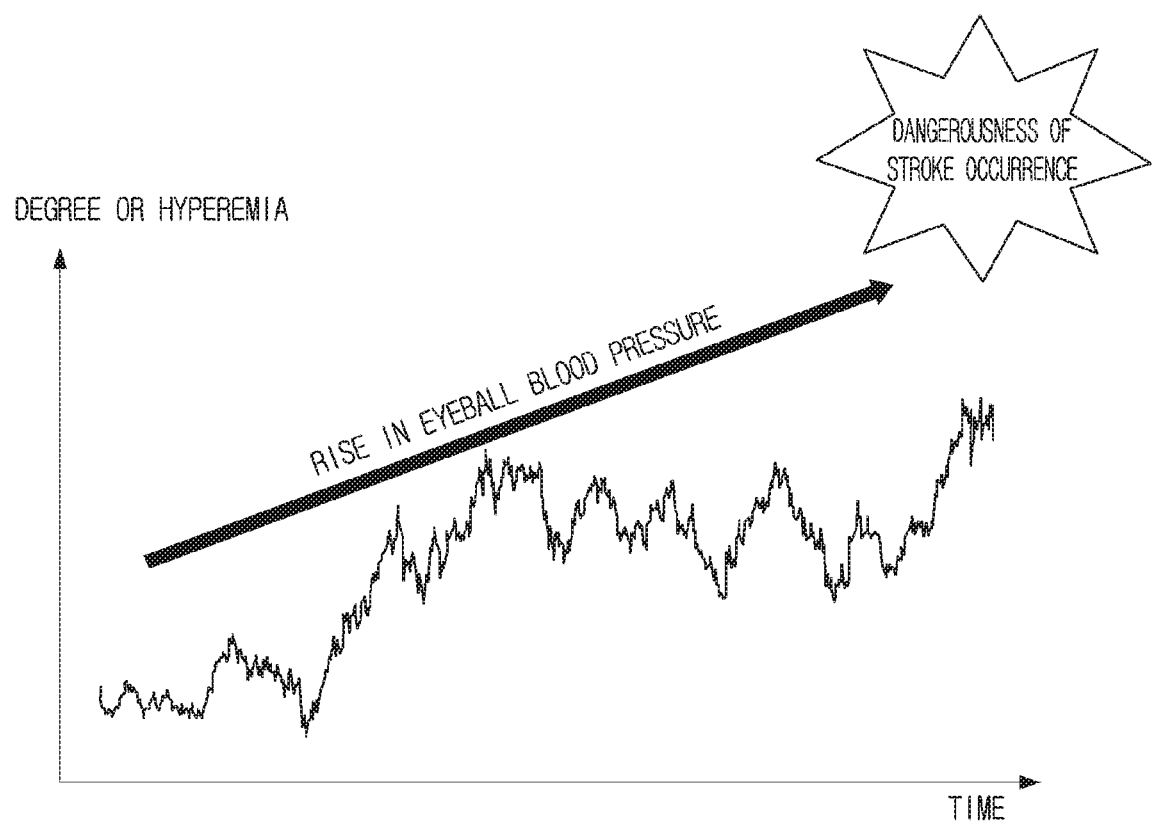
FIG. 18 is a diagram illustrating an embodiment of providing a change in the degree of hyperemia in a predetermined time unit according to an embodiment.

FIG. 18 is a diagram illustrating an embodiment of providing a change in the degree of hyperemia in a predetermined time unit according to an embodiment. The processor 120 may store the degree of conjunctival hyperemia determined through the captured image on a storage (not shown).

The processor 120 can determine a change of the degree of hyperemia by a predetermined time unit based on the degree of hyperemia information stored in the storage. For example, the processor 120 may determine a change in the degree of hyperemia in a unit of 24 hours, but is not necessarily limited thereto. As an example, the processor 120 may determine a change in the degree of hyperemia in various units, such as one minute, ten minutes, one hour, or the like.

As the graph of FIG. 18, the processor 120 may provide a change in the degree of hyperemia on a time unit basis.

The processor 120 may provide guide information for managing the degree of hyperemia, if the change in the degree of hyperemia is greater than or equal to a predetermined changing amount. For example, if the degree of hyperemia determined at the second time is higher than the degree of hyperemia determined at the first time, the processor 120 may provide guide information guiding the rest of the eye.

In addition, the processor 120 may provide feedback to the user to inform the user of the dangerousness of the ocular disease if it is determined that the user's degree of hyperemia is continuously increasing. Here, the feedback can be an alarm sound output through audio, as well as visually indicating the information that the degree of conjunctival hyperemia is continually increasing.

The processor 120 may continue to provide feedback to the user that cerebrovascular disease, such as stroke, may occur due to ocular blood pressure rise, if it is determined that the degree of hyperemia of a user is continually increasing even after providing feedback to the user to inform the user of the dangerousness of ocular disease.

Thus, the processor 120 may notify a user of the dangerousness of hyperemia and induce an action to improve health of the eye.

Figure 19:
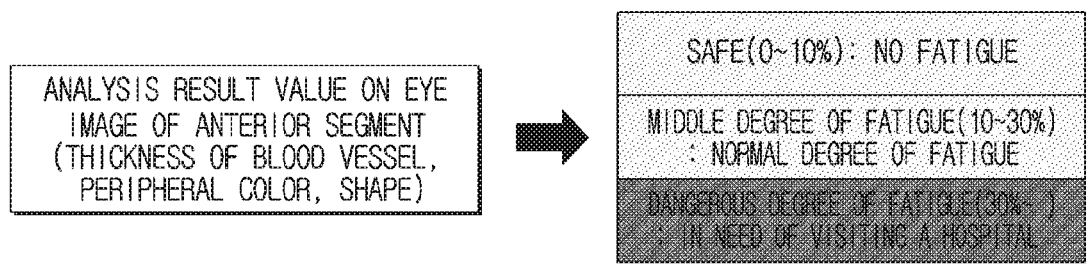
FIG. 19 is a view illustrating an embodiment of providing information related to a level of fatigue based on the degree of hyperemia according to an embodiment.

FIG. 19 is a view illustrating an embodiment of providing information related to a level of fatigue based on the degree of hyperemia according to an embodiment.

The processor 120 may classify the determined degree of hyperemia according to predetermined criteria, and determine the fatigue of the user. More specifically, the processor 120 can determine the fatigue degree of the user as being low when the determined degree of hyperemia is less than or equal to a first threshold value, and can determine the fatigue of the user as being a middle if the determined degree of hyperemia exceeds the first threshold value and is less than or equal to the second threshold value, and can determine the fatigue of the user as being serious when the determined degree of hyperemia exceeds the second threshold value. For example, referring to FIG. 10, the first threshold value may be the case where degree of hyperemia is 10%, and the second threshold value may be the case where the degree of hyperemia is 30%

In addition, if it is determined that the fatigue of the user is the middle, the processor 120 can display guide information guiding the rest and display guide information for guiding the hospital visit if the fatigue of the user is determined to be serious. Accordingly, the disclosure can induce a user to manage the health of the eye.

Figure 20:
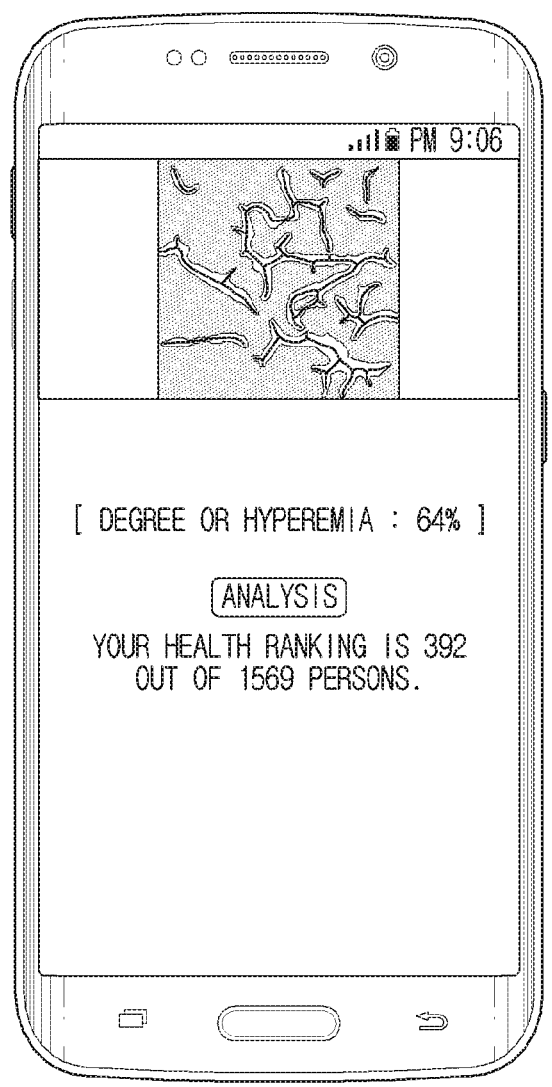
FIG. 20 is a diagram illustrating an embodiment of displaying ranking of the degree of hyperemia of a user according to an embodiment.

FIG. 20 is a diagram illustrating an embodiment of displaying ranking of the degree of hyperemia of a user according to an embodiment.

Referring to FIG. 20, the processor 120 may provide the ranking information of the degree of conjunctival hyperemia determined through the captured image.

For this purpose, the processor 120 may receive information on the degree of hyperemia of a plurality of users from a server, compare the degree of conjunctival hyperemia information of the plurality of users with the degree of conjunctival hyperemia determined through the captured image, to determine the ranking of the degree of conjunctival hyperemia determined through the captured image.

For this purpose, the electronic device 100 may further include a communicator (not shown) for communicating with a server. The communicator (not shown) may include a Wi-Fi chip, a Bluetooth chip, a wireless communication chip, or the like.

The processor 120 may provide a ranking of the user's degree of hyperemia, within a group to which the user belongs. For this purpose, the processor 120 may first determine a user corresponding to the eye based on the user identification information. Here, the user identification information can be user ID information as described above.

The processor 120 may receive information on at least one of age and occupation of each of the plurality of users from the server, divide the plurality of users into a plurality of groups based on at least one of age and occupation, and determine a group to which the identified user of the plurality of groups belongs.

The processor 120 may compare the degree of conjunctival hypermedia formation of the plurality of users belonging to the determined group and the degree of conjunctival hypermedia determined through the captured image to determine the ranking of the degree of conjunctival hyperemia determined through the captured image and provide information on the ranking.

Accordingly, the user may receive a feedback regarding whether the degree of conjunctival hyperemia is high or low as compared to the plurality of users in the same occupation or same age.

Figure 21:
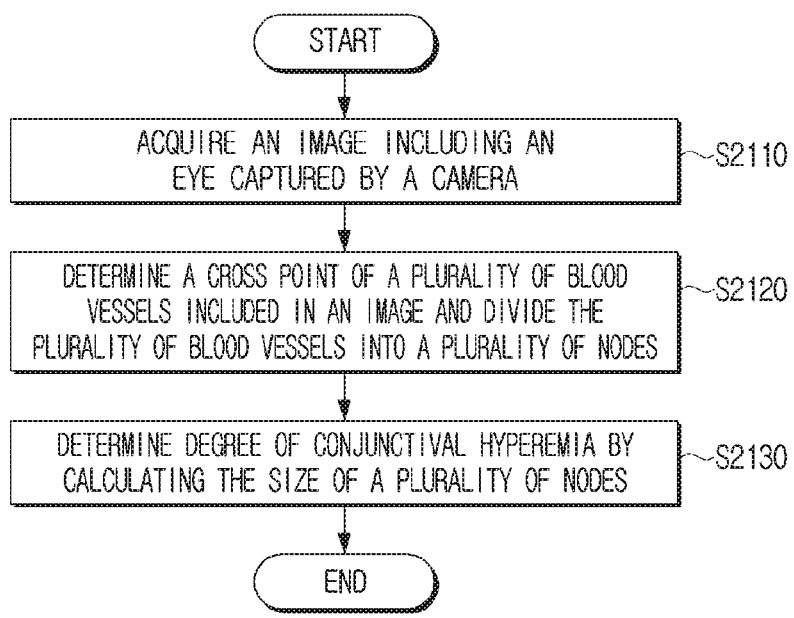
FIG. 21 is a flowchart illustrating a method for determining the degree of conjunctival hyperemia by an electronic device according to an embodiment.

FIG. 21 is a flowchart illustrating a method for determining the degree of conjunctival hyperemia by an electronic device according to an embodiment.

According to an embodiment, the electronic device can obtain an image including an eye when the eye is captured through a camera. In addition, the electronic device can obtain an anterior section image from the image including the eye, and can acquire the sclera image from the anterior section image in operation S2110.

The electronic device may perform image processing for the sclera image to determine the cross point of the plurality of blood vessels. The electronic device may adjust the contrast of the sclera image by using the CLAHE algorithm, binarize the sclera image in which the contrast is adjusted, and obtain a plurality of blood vessels from the binarized image. The electronic device can determine the cross point of a plurality of blood vessels by converting the thickness of the acquired plurality of blood vessels into a thickness in a predetermined unit.

The electronic device may divide the plurality of blood vessels into a plurality of nodes based on a cross point of the plurality of blood vessels in operation S2120. The node can be a vessel between the cross point of the plurality of vessels and the end point of each of the plurality of blood vessels based on the cross point.

The electronic device can calculate the size of the plurality of nodes to determine the degree of conjunctival hyperemia in operation S2130. Specifically, the electronic device may obtain the sclera region of a predetermined unit area in the sclera image, calculate the size of the plurality of nodes based on the cross point of the plurality of blood vessels included in the sclera region, and compare the sum of the calculated sizes of the plurality of nodes and the predetermined unit area to determine the degree of conjunctival hyperemia.

Figure 22:
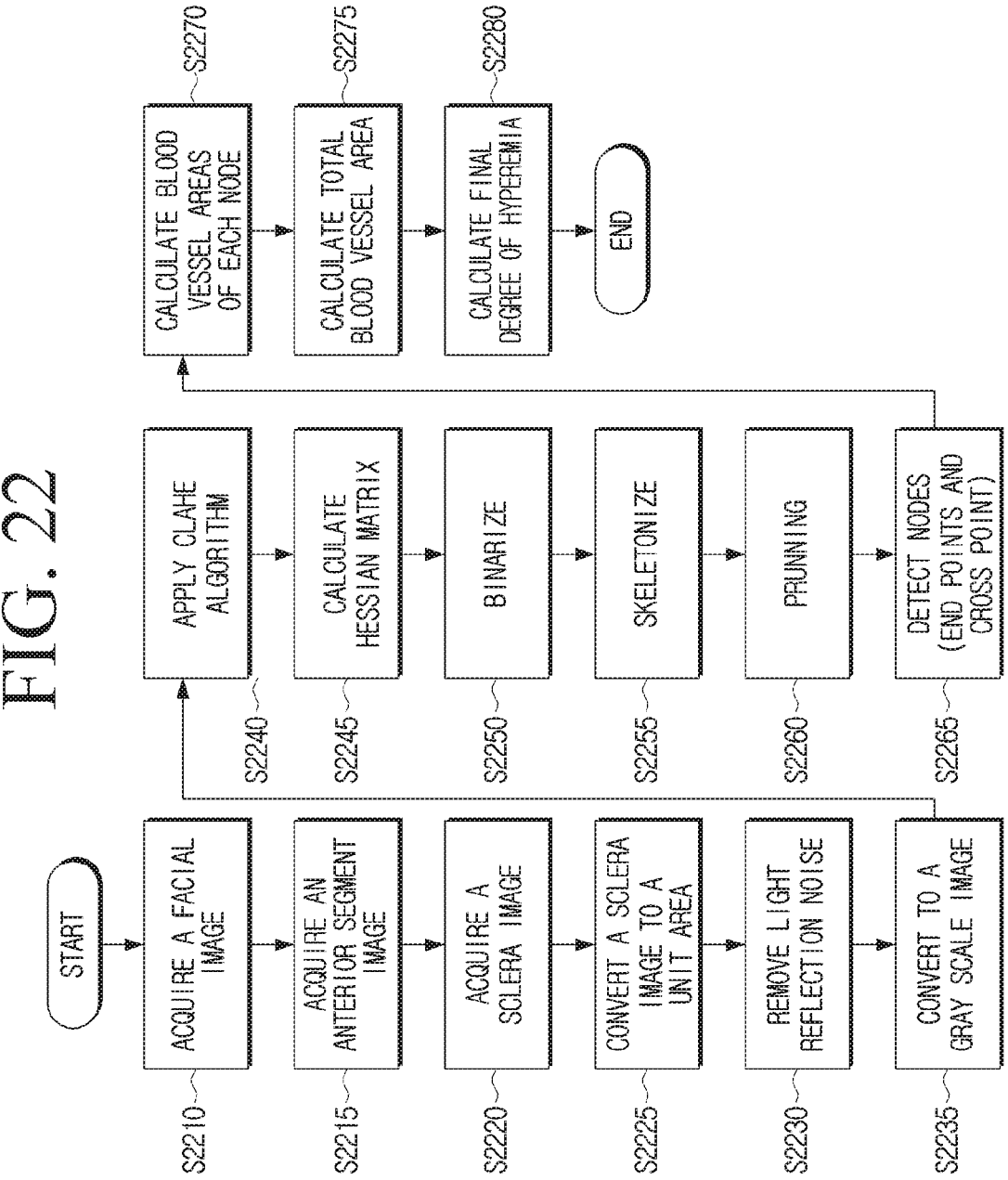
FIG. 22 is a flowchart illustrating a method for determining the degree of conjunctival hyperemia by an electronic device according to an embodiment.

FIG. 22 is a flowchart illustrating a method for determining the degree of conjunctival hyperemia by an electronic device according to an embodiment.

First, the electronic device may obtain a facial image that includes the user's eye in operation S2210. The facial image may include eyes, nose and mouth of the user. The electronic device can obtain an anterior image in the facial image in operation S2215. For example, the electronic device can obtain the anterior section image by using location information such as eyes, nose mouth, etc. included in the facial image.

The electronic device may acquire the sclera image from the anterior section image in operation S2220. For example, the electronic device may acquire the sclera image through analysis of the anterior segment image or database or deep learning technology based on deep learning.

The electronic device can convert the sclera image into a predetermined unit area in operation S2225. The predetermined unit area may be determined by considering the size of a general user's sclera. In one example, the predetermined unit area may be a square area of 30 mm in width and 30 mm in length. However, the predetermined unit area may be changed according to a user setting, without limitation.

When the reflected light is included in the sclera image, the electronic device may remove the reflected light in operation S2230. This considers whether there is a blood vessel in a position where the reflected light is present may not be determined.

The electronic device can perform image processing for the sclera image converted in a unit area. Specifically, the electronic device may convert the sclera image into a gray-scale image in operation S2235, apply the CLAHE algorithm to the image converted into the gray-scale image in operation S2240, and apply a Hessian matrix to an image to which the CLAHE algorithm is applied in operation S2245, to adjust the contrast of the sclera image and highlight the blood vessel.

The electronic device may binarize the image-processed sclera image in operation S2250. Accordingly, the electronic device can obtain a plurality of blood vessels in the sclera image. The electronic device may convert the plurality of blood vessels obtained from the binarized image into a predetermined thickness in operation S2255.

The electronic device can apply pruning to a plurality of blood vessels converted to a predetermined thickness in operation S2260. The pruning can refer to a task of cutting a plurality of blood vessels. Specifically, the electronic device can divide a single blood vessel into a plurality of unit blood vessels by pruning a plurality of blood vessels.

The electronic device may determine the cross points of the plurality of unit blood vessels for which pruning is performed and the end points of each unit blood vessel in operation S2265. The electronic device may determine a point where different unit blood vessels cross as a cross point.

Thereafter, the electronic device may divide the plurality of blood vessels into a plurality of nodes based on the cross points of the plurality of vessels. Here, the node can mean a blood vessel between the cross points at which the plurality of blood vessels cross and end points of each of the plurality of blood vessels relative to the cross points.

The electronic device can calculate the blood vessel size of each node in operation 52270t. In one example, the electronic device can calculate the blood vessel size of each mast through a point-counting method. The electronic device can calculate a total blood vessel area in operation S2275 by summing the blood vessel sizes of each node, and can calculate a final degree of hyperemia in operation S2280 by comparing with the area of the sclera image.

The methods according to various example embodiments as described above may be implemented as a software or an application format which may be installed in an existing electronic apparatus.

The methods according to various example embodiments as described above may be implemented by software upgrade and/or hardware upgrade for the existing electronic apparatus.

The various example embodiments as described above may be performed through an embedded server provided in the electronic apparatus or an external server of the electronic apparatus.

A non-transitory computer readable medium having a program for sequentially performing a method for calculating the degree of hyperemia stored therein may be provided.

The non-transitory computer readable medium refers to a medium that stores data semi-permanently rather than storing data for a very short time, such as a register, a cache, a memory or etc., and is readable by an apparatus. In detail, the aforementioned various applications or programs may be stored in the non-transitory computer readable medium, for example, a compact disc (CD), a digital versatile disc (DVD), a hard disc, a Blu-ray disc, a universal serial bus (USB), a memory card, a read only memory (ROM), and the like, and may be provided.

While various embodiments have been illustrated and described with reference to certain drawings, the disclosure is not limited to specific embodiments or the drawings, and it will be understood by those of ordinary skill in the art that various changes in form and details may be made therein without departing from the spirit and scope as defined, for example, by the following claims and their equivalents.

What is claimed is:

1. An electronic device comprising:
a camera; and
a processor configured to:
    obtain an image, including an eye, captured by the camera,
    identify a plurality of blood vessels included in the image, and
    determine a degree of conjunctival hyperemia based on sizes of the identified plurality of blood vessels,
wherein the processor is configured to divide the plurality of blood vessels into a plurality of nodes based on corss points of the plurality of blood vessels included in the image, and determine the degree of conjunctival hyperemia based on sizes of the plurality of nodes, and
wherein the plurality of nodes comprises at least one of a blood vessel between a first cross point and end points of blood vessels with repsect to the first cross point or a blood vessel between the first cross point and another second cross point.

2. The electronic device of claim 1, wherein the processor is configured to:
calculate a hessian matrix of the image,
apply the hessian matrix to the image,
identify the plurality of blood vessels by binarizing the image to which the hessian matrix is applied,
determine the cross points by converting thickness of the plurality of blood vessels to thickness of a predetermined unit, and
calculate the sizes of each of the plurality of nodes from the binarized image.

3. The electronic device of claim 1, wherein the processor is configured to:
acquire a sclera image in a predetermined unit area in the image,
calculate sizes of the plurality of nodes based on cross points of the plurality of blood vessels included in the sclera image, and
determine the degree of conjunctival hyperemia by comparing a sum of the calculated sizes of the plurality of nodes and the predetermined unit area.

4. The electronic device of claim 1, wherein the processor is configured to determine locations of the plurality of nodes in the image and determine the degree of hyperemia by parts of the eye based on locations in which the plurality of nodes are present.

5. The electronic device of claim 1, wherein the processor is configured to:
determine the degree of conjunctival hyperemia by determining a thickness of the plurality of nodes,
acquiring at least one node, among the plurality of nodes, having a thickness greater than or equal to a predetermined thickness, and
calculating a size of the acquired at least one node, or
determine the degree of conjunctival hyperemia by acquiring at least one node, among the plurality of nodes, having a thickness less than a predetermined thickness and calculating a size of the acquired at least one node.

6. The electronic device of claim 1, wherein the processor is configured to, based on a reflected light being included in the image, determine a remaining region, among the entire regions of the image, other than the region including the reflected light, and determine the degree of conjunctival hyperemia based on a size of one or more blood vessels included in the remaining region.

7. The electronic device of claim 1, wherein the processor is configured to determine the degree of hyperemia by determining a remaining region other than the identified plurality of blood vessels from the image and further considering at least one of a color or a shape of the remaining region.

8. The electronic device of claim 1, wherein the processor is configured to sequentially provide an image captured by the camera, an image including the plurality of blood vessels divided into the plurality of nodes based on the cross points, and an image of the determined degree of hyperemia.

9. The electronic device of claim 1, wherein:
an eye image captured by the camera comprises a left eye and a right eye of a user,
the processor is configured to:
based on a distance between the left eye and the right eye being less than a predetermined distance, provide guide information guiding the user to be positioned in proximity to the camera, and
based on the distance between the left eye and the right eye included in the eye image being a predetermined distance, determine the degree of hyperemia.

10. The electronic device of claim 1, further comprising:
an illuminance sensor,
wherein the processor is configured to:
based on an illuminance value sensed by the illuminance sensor being less than or equal to a predetermined illuminance value, provide guide information guiding adjustment of the illuminance value, and
based on the illuminance value being greater than or equal to a predetermined illuminance value, determine the degree of conjunctival hyperemia included in the image.

11. The electronic device of claim 1, wherein:
the processor is configured to provide at least one of a cause of the degree of hyperemia and guide information for overcoming the degree of hyperemia based on at least one of state information of the electronic device, user information, the degree of hyperemia,
the state information of the electronic device comprises at least one of a distance between the electronic device and the user, a slope of the electronic device, an ambient illuminance of the electronic device, or time for using the electronic device, and
the user information is generated based on at least one of a photo application or a schedule application stored in the electronic device.

12. The electronic device of claim 1, further comprising:
a storage,
wherein the processor is configured to:
determine a change in the degree of hyperemia in a predetermined time unit based on information on the degree of hyperemia stored in the storage and, based on the change in the degree of hyperemia being greater than or equal to a predetermined change amount, provide guide information for managing the degree of hyperemia.

13. The electronic device of claim 1, wherein the processor is configured to, based on an iris authentication application being executed, capture an image including the eye through the camera and determine the degree of conjunctival hyperemia from the captured image.

14. A method for determining a degree of conjunctival hyperemia, the method comprising:
obtaining an image, including an eye, that is captured by a camera;
identifying a plurality of blood vessels included in the image; and
determining the degree of conjunctival hyperemia based on a size of the identified plurality of blood vessels,
wherein the method further comprises dividing the plurality of blood vessels into a plurality of nodes based on cross points of the plurality of bloode vessels included in the image, and determining the degree of conjunctival hyperemia based on sizes of the plurality of nodes, and,
wherein the plurality of nodes comprises at least one of a blodd vessel between a first cross point and end points of blood vessels with respect to the first cross point or a blood vessel between the first cross point and another second cross point.

15. The method of claim 14, further comprising:
calculating a hessian matrix of the image,
applying the hessian matrix to the image,
identifying the plurality of blood vessels by binarizing the image to which the hessian matrix is applied,
determining the cross points by converting thicknesses of the plurality of blood vessels to thicknesses of a predetermined unit, and
calculating the sizes of each of the plurality of nodes from the binarized image.

16. The method of claim 14, further comprising:
acquiring a sclera image in a predetermined unit area in the image,
calculating sizes of the plurality of nodes based on cross points of the one or more blood vessels included in the sclera image, and
determining the degree of conjunctival hyperemia by comparing a sum of the calculated sizes of the plurality of nodes and the predetermined unit area.

17. The method of claim 14, further comprising determining locations of the plurality of nodes in the image and determining the degree of hyperemia by parts of the eye based on locations in which the plurality of nodes are present.

18. A non-transitory computer readable medium storing a program which, when executed, causes an electronic device to determine a degree of conjunctival hyperemia by controlling the electronic device to perform operations comprising:
obtaining an image, including an eye, that is captured by a camera;
identifying a plurality of blood vessels included in the image; and
determining the degree of conjunctival hyperemia based on a size of the identified plurality of blood vessels,
wherein the operations further comprise dividing the plurality of blood vessels into a plurality of nodes based on cross points of the plurality of blood vessels included in the image, and determining the degree of conjunctival hyperemia based on sizes of the plurality of nodes, and
wherein the plurality of nodes comprises at least one of a blood vessel between a first cross point and end points of blood vessels with respect to the first cross point or a blood vessel between the first cross point and another second cross point.

* * * * *